US011440968B2

(12) United States Patent
Terme et al.

(10) Patent No.: US 11,440,968 B2
(45) Date of Patent: Sep. 13, 2022

(54) HUMANIZED ANTIBODY AGAINST O-ACETYLATED GD2 GANGLIOSIDE (OACGD2)

(71) Applicant: OGD2 PHARMA, Nantes (FR)

(72) Inventors: Mickaël Terme, Nantes (FR); Jean-Marc Le Doussal, Lausane (CH); Mylene Dorvillius, Bouguenais (FR); Brigitte Assouline, Courbevoie (FR)

(73) Assignee: OGD2 PHARMA, Nantes (FR)

( * ) Notice: Subject to any disclaimer, the term of this patent is extended or adjusted under 35 U.S.C. 154(b) by 400 days.

(21) Appl. No.: 16/317,972

(22) PCT Filed: Jul. 17, 2017

(86) PCT No.: PCT/EP2017/000855
§ 371 (c)(1),
(2) Date: Jan. 15, 2019

(87) PCT Pub. No.: WO2018/010846
PCT Pub. Date: Jan. 18, 2018

(65) Prior Publication Data
US 2019/0233537 A1 Aug. 1, 2019

(30) Foreign Application Priority Data
Jul. 15, 2016 (EP) ..................................... 16001564

(51) Int. Cl.
*C07K 16/30* (2006.01)
*G01N 33/574* (2006.01)

(52) U.S. Cl.
CPC ... *C07K 16/3084* (2013.01); *G01N 33/57469* (2013.01); *C07K 2317/24* (2013.01); *C07K 2317/56* (2013.01); *C07K 2317/565* (2013.01); *C07K 2317/622* (2013.01); *C07K 2317/73* (2013.01); *C07K 2317/92* (2013.01)

(58) Field of Classification Search
CPC ............ C07K 16/3084; C07K 2317/56; C07K 2317/565; C07K 2317/73; C07K 2317/24; C07K 2317/622; C07K 2317/92; G01N 33/57469; A61P 35/02; A61P 35/00; A61P 27/02; A61P 25/00; A61P 21/00; A61P 17/00; A61P 15/00; A61P 13/12; A61P 11/00
See application file for complete search history.

(56) References Cited

U.S. PATENT DOCUMENTS

| 4,690,915 | A | 9/1987 | Rosenberg |
|---|---|---|---|
| 5,730,969 | A | 3/1998 | Hora et al. |
| 8,951,524 | B2 | 2/2015 | Birkle et al. |
| 10,000,575 | B2 | 6/2018 | Birkle et al. |
| 10,167,341 | B2 | 1/2019 | Cheung et al. |
| 2016/0272722 | A1 | 9/2016 | Le Doussal et al. |
| 2017/0226183 | A1 | 8/2017 | Schiffer-Mannioui |

FOREIGN PATENT DOCUMENTS

| EP | 2 871 190 A1 | 5/2015 |
|---|---|---|
| WO | 2008/043777 A1 | 4/2008 |
| WO | 2014/144763 A2 | 9/2014 |
| WO | 2014/177271 A1 | 11/2014 |
| WO | 2016/016343 A1 | 2/2016 |

OTHER PUBLICATIONS

Edwards et al, J Mol Biol 334:103-118 (2003) (Year: 2003).*
Marchalonis et al., Dev & Comp Immunol 30:223-247 (2006) (Year: 2006).*
Almagro & Fransson, Frontiers in Bioscience 2008; 13:1619-33 (Year: 2008).*
Cheung, FEBS Letters 588 (2014) 288-297 (Year: 2014).*
Sela-Culang, et al., Frontiers in Immunology 2013 vol. 4 Article 302 (Year: 2013).*
Terme et al., "Chimeric Antibody c.8B6 to O-Acetyl-GD2 Mediates the Same Efficient Anti-Neuroblastoma Effects as Therapeutic ch14. 18 Antibody to GD2 without Antibody Induced Allodynia", PLOS One, 2014, Article No. e87210, vol. 9, No. 2.
Alvarez-Rueda et al., "A Monoclonal Antibody to O-Acetyl-GD2 Ganglioside and Not to GD2 Shows Potent Anti-Tumor Activity without Peripheral Nervous System Cross-Reactivity", PLOS One, 2011, Article No. e25220, vol. 6, No. 9.
Fleurence et al., "Targeting and killing glioblastoma with monoclonal antibody to O-acetyl GD2 ganglioside", Oncotarget, 2016, pp. 41172-41185, vol. 7, No. 27.
Zhao et al., "Alteration of electrostatic surface potential enhances affinity and tumor killing properties of antiganglioside GD2 monoclonal antibody hu3F8", Journal of Biological Chemistry, 2015, pp. 13017-13027, vol. 290, No. 21.
Ahmed et al., "In silico Driven Redesign of a Clinically Relevant Antibody for the Treatment of GD2 Positive Tumors", PLOS One, 2013, Article No. e63359, vol. 8, No. 5.
International Search Report and Written Opinion, dated Oct. 13, 2017, from corresponding PCT application No. PCT/EP2017/000855.
L. K. Gilliland et al., "Rapid and reliable cloning of antibody variable regions and generation of recombinant single chain antibody fragments", Tissue Antigens, Jan. 1996, vol. 47, No. 1, pp. 1-20 (20 pp.), doi: 10.1111/j.1399-0039.1996.tb02509.x.

(Continued)

*Primary Examiner* — Julie Wu
*Assistant Examiner* — John L Van Druff
(74) *Attorney, Agent, or Firm* — Nixon & Vanderhye

(57) ABSTRACT

Disclosed is an antibody, functional fragment, and derivative thereof, which binds specifically to the OAcGD2 ganglioside, the antibody including i) a humanized light chain variable region (VL) polypeptide having the amino acid sequence SEQ id no 112; and ii) a humanized heavy chain variable region (VH) having the amino acid sequence SEQ id no 76; and its use in diagnostics and therapy.

21 Claims, 3 Drawing Sheets
Specification includes a Sequence Listing.

(56) References Cited

OTHER PUBLICATIONS

Temple F. Smith and Michael S. Waterman, "Comparison of biosequences", Advances in Applied Mathematics, Dec. 1981, vol. 2, No. 4, pp. 482-489 (8 pp.), https://doi.org/10.1016/0196-8858(81)90046-4.

Saul B. Needleman and Christian D. Wunsch, "A general method applicable to the search for similarities in the amino acid sequence of two proteins", Journal of Molecular Biology, Mar. 1970, vol. 48, No. 3, pp. 443-453 (11 pp.), doi: 10.1016/0022-2836(70)90057-4.

William R. Pearson and David J. Lipman, "Improved tools for biological sequence comparison", Proc. Natl. Acad. Sci. USA, Apr. 1988, vol. 85, No. 8, pp. 2444-2448 (5 pp.), doi: 10.1073/pnas.85.8.2444.

Robert C. Edgar, "Muscle: multiple sequence alignment with high accuracy and high throughput", Nucleic Acids Research, Mar. 19, 2004, vol. 32, No. 5, pp. 1792-1797 (6 pp.), doi: 10.1093/nar/gkh340.

Deborah Finco et al., "Cytokine release assays: current practices and future directions", Cytokine, Apr. 2014, vol. 66, No. 2, pp. 143-155 (13 pp.), doi: 10.1016/j.cyto.2013.12.009.

Denis Cochonneau et al., "Cell cycle arrest and apoptosis induced by O-acetyl-GD2-specific monoclonal antibody 8B6 inhibits tumor growth in vitro and in vivo", Cancer Letters, Jun. 10, 2013, vol. 10, No. 2, pp. 194-204 (11 pp.), doi: 10.1016/j.canlet.2013.01.032.

Kerry Parsons et al., "Targeted immunotherapy for high-risk neuroblastoma—the role of monoclonal antibodies", Annals of Pharmacotherapy, Feb. 2013, vol. 47, No. 2, pp. 210-218 (9 pp.), doi: 10.1345/aph.1R353.

Marie-Paule Lefranc et al., "IMGT, The International Immunogenetics database", Nucleic Acids Research, Jan. 1, 1999, vol. 27, No. 1, pp. 209-212 (4 pp.), doi: 10.1093/nar/27.1.209.

Cyrus Chothia and Arthur M. Lesk, "Canonical structures for the hypervariable regions of immunoglobulins", Journal of Molecular Biology, Aug. 20, 1987, vol. 196, No. 4, pp. 901-917 (17 pp), doi: 10.1016/0022-2836(87)90412-8.

Cheung et al., "Humanizing murine IgG3 anti-GD2 antibody m3F8 substantially improves antibody-dependent cell-mediated cytotoxicity while retaining targeting in vivo," Oncolmmunology, Jul. 2012, vol. 1, No. 4, pp. 477-486, doi: 10.4161/onci.19864.

Ahmed et al., "Structure Based Refinement of a Humanized Monoclonal Antibody That Targets Tumor Antigen Disialoganglioside GD2," Frontiers in immunology, Aug. 14, 2014, vol. 5, Article 372, 6 pages, doi: 10.3389/fimmu.2014.00372.

* cited by examiner

HUMANIZED ANTIBODY AGAINST O-ACETYLATED GD2 GANGLIOSIDE (OACGD2)

The present patent application claims the priority of the European patent application EP16001564.0 filed on Jul. 15, 2016, which is herein incorporated by reference.

FIELD OF THE INVENTION

The present invention provides novel antibodies and their uses in cancer therapies and diagnosis.

BACKGROUND OF THE INVENTION

GD2, a disialoganglioside, is an oncofetal antigen that is expressed in the fetus, which is also found in neural stem cells, and mesenchymal stem cells.

Ganglioside GD2 is also a tumor-associated surface antigen found in a broad spectrum of human cancers and stem cells including neuroblastoma, glioma, retinoblastoma, Ewing's family of tumors, rhabdomyosarcoma, osteosarcoma, leiomyosarcoma, liposarcoma, fibrosarcoma, small cell lung cancer and melanoma. Nevertheless, it is also found on stem cells, neurons, some nerve fibers and basal layer of the skin.

On this basis, the antibody dinutuximab (UNITED THERAPEUTICS) directed against GD2 has been authorized by the FDA and EMA, and recently the antibody dinutuximab beta (APEIRON) has been recently authorized by the EMA, which are both for the treatment of neuroblastoma. However, dinutuximab given in combination with granulocyte-macrophage colony-stimulating factor (GM-CSF), interleukin 2 (IL-2) and isotretinoin (RA) induce severe side effects especially intense neuropathic pain in 85% of patients (despite pretreatment with analgesics including morphine sulfate infusion), serious sensory and motor neuropathies related to the expression of GD2 on nerve and brain cells. Severe (Grade 3) pain occurred in 52% vs. 5% of patients when compared to standard treatment with isotretinoin. Toxicity to central nervous system has also been reported and is worrisome to clinicians. Now, because of its neurotoxicity, its use has been restricted to high-risk neuroblastoma in pediatric patients.

This on-target toxicity is highly detrimental to patient quality of life, limits the efficacy of anti-GD2 therapy, and impairs the development of next generation immunotherapies targeting GD2 positive cancer. Despite significant advances in neuroblastoma treatment, high-risk NB is associated with a poor prognosis, and there is a strong need for more effective and less-toxic drugs and strategies to treat NB and other cancer.

It has been previously demonstrated that a modified form of GD2—i.e. O-acetylated GD2 ganglioside (OAcGD2)—has, in contrast to GD2, a safer expression pattern, with no expression in the peripheral nerves, pituitary gland or human brain cells but, as GD2, OAcGD2 is expressed on tumors. As a result, it has been shown in the international patent application PCT WO 2008/043777 that the administration of a mouse therapeutic antibody (8B6) targeting this OAcGD2 is not associated with any neurotoxicity, especially due to the absence of expression of this cancer antigen on healthy cells, notably on peripheral nerves. A human-mouse chimeric antibody, named c8B6, have been first generated. This specific antibody shows no cross-reaction, neither with GD2, nor with others gangliosides and shows the absence of OAcGD2 antigen expression in the normal brain tissue. In animal models, anti-OAcGD2 chimeric antibodies display similar anti-tumor activity than anti-GD2 monoclonal antibodies (mAbs), while avoiding their toxicity, indicating that OAcGD2 is a better tumor-associated antigen than GD2 and that anti-OAcGD2 mAbs are best-in-class antibodies capable to reduce the uncomfortable side effects commonly associated with anti-GD2 mAb therapies and improve quality of life of patients. However, chimeric antibodies may cause immunogenicity and reduce anti-OAcGD2 efficiency. This problem may be overcome by generating "human", "humanized' or "humaneered" antibodies. Now, humanized anti-OAcGD2 antibodies are needed.

Humanized antibodies generally have at least three potential advantages over mouse or in some cases chimeric antibodies for use in human therapy:

(1) Because the effector portion is human, it may interact better with the other parts of the human immune system (e.g., destroy the target cells more efficiently by complement-dependent cytotoxicity (CDC) or antibody-dependent cellular cytotoxicity (ADCC));

(2) The human immune system should not recognize the framework or constant region of the humanized antibody as foreign, and therefore the antibody response against such an injected antibody should be less than against a totally foreign mouse antibody or a partially foreign chimeric antibody; and (3) Injected mouse antibodies have been reported to have a half-life in the human circulation much shorter than the half-life of human antibodies. Injected humanized antibodies will presumably have a half-life more similar to naturally occurring human antibodies, allowing smaller and less frequent doses to be given.

Nevertheless, the obtaining of humanized antibody is not so simple since humanization process results most of the time in loss of antigen binding affinity and/or loss of specificity. As CDR regions confer both affinity and specificity for antigen, the modification of these regions to reduce potential immunogenicity might be problematic.

Thus, the antibody humanization has to be designed so as to retain specificity and affinity of the antibody for the antigen, while producing molecule with minimal immunogenicity in humans.

Now, this process is so complex that the obtaining of such humanized antibody is never evident.

SUMMARY OF THE INVENTION

Now, the inventors have surprisingly shown that only specific substitutions maintain the binding affinity, whether the immunogenicity of the antibody is improved or potentially improved. Thus, the inventors provide with new humanized anti-OAcGD2 antibodies (OGD201) with such substitutions.

Consequently, the present invention relates to an antibody, functional fragment, and derivative thereof, which binds specifically to the OAcGD2 ganglioside, said antibody comprising:
  a) a humanized light chain variable region (VL) polypeptide having the amino acid sequence SEQ ID NO:112; and
  b) a humanized heavy chain variable region (VH) having the amino acid sequence SEQ ID NO:76.

The present invention also relates to a pharmaceutical composition comprising at least one of such antibody, and a pharmaceutically acceptable carrier.

Additionally, the present invention relates to a method for treating and/or preventing a cancer expressing the OAcGD2 comprising providing to a patient in need thereof such a pharmaceutical composition which comprises at least one said antibody, or at least one functional fragment or derivative thereof.

The present invention relates to a pharmaceutical composition comprising at least one of such antibody, or at least one such functional fragment or derivative thereof for use in a method for treating and/or preventing cancer expressing the OAcGD2 ganglioside.

The present invention relates to a method for diagnosing a cancer expressing the OAcGD2 ganglioside in a subject comprising the step of contacting a biological sample of said subject with at least one antibody as described herein, functional fragment, or derivative thereof, for determining the OAcGD2 ganglioside expression level in said biological sample, wherein a detectable OAcGD2 expression level is indicative of such a cancer.

Finally, the present invention relates to a kit for diagnosing a cancer expressing the OAcGD2 ganglioside in a subject, which comprises at least one of such antibody, or at least one such functional fragment or derivative thereof.

DETAILED DESCRIPTION

Figure 1:
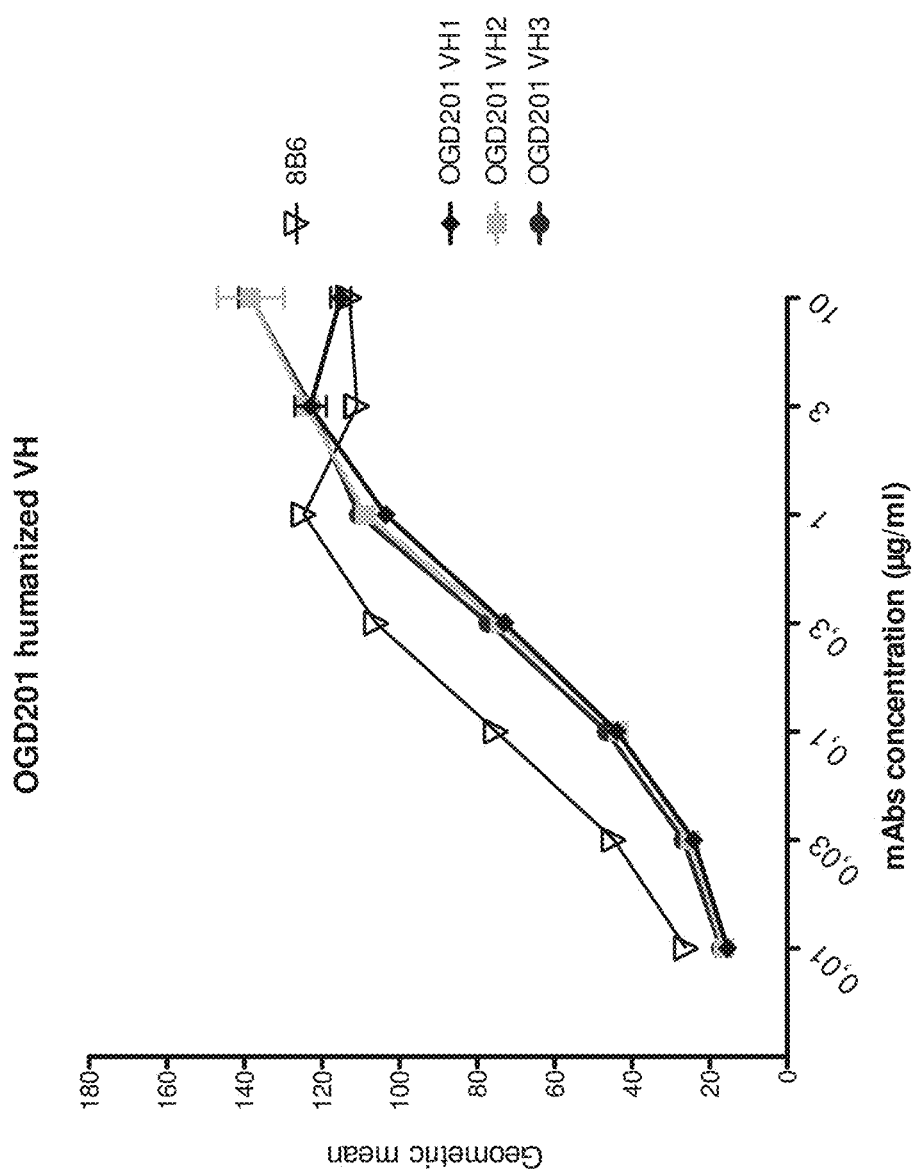
FIG. 1 presents the binding titration assays on IMR5 cells of VH humanized anti-OAcGD2 (8B6 VL) mAb as compared to the mouse antibody.

In a first aspect, the present invention concerns an antibody, functional fragment, and derivative thereof, which binds specifically to the OAcGD2 ganglioside, said antibody comprising:

a) a humanized light chain variable region (VL) polypeptide having the amino acid sequence SEQ ID NO:112; and b) a humanized heavy chain variable region (VH) having the amino acid sequence SEQ ID NO:76.

In a first preferred embodiment, the humanized light chain variable region (VL) polypeptide is selected in the group comprising VL30BH (SEQ ID NO:134) and VL28Bs01/A2 (SEQ ID NO:135).

Preferably, the humanized heavy chain variable region (VH) polypeptide is selected in the group comprising VH72Bmax (SEQ ID NO:131), VH49B (SEQ ID NO:132), and VH49Bmax (SEQ ID NO:133).

In fact, the inventors surprisingly established that VH72Bmax, VH49B, VH49Bmax, VL30BH, and VL28Bs01/A2 have both a binding affinity comparable to their mouse counterpart, and a weaken immunogenicity.

In a second preferred embodiment, the humanized light chain variable region (VL) polypeptide is selected in the group comprising VL1 (SEQ ID NO:8), VL2 (SEQ ID NO:9), VL3 (SEQ ID NO:10), VL4 (SEQ ID NO:11), VL28BH (SEQ ID NO:140), VL30BH (SEQ ID NO:134) and VL28Bs01/A2 (SEQ ID NO:135).

Preferably, the humanized heavy chain variable region (VH) polypeptide is selected in the group comprising VH1 (SEQ ID NO:3), VH2 (SEQ ID NO:4), and VH3 (SEQ ID NO:5), VH72BCDR (SEQ ID NO:136), VH72BH (SEQ ID NO:137), VH49BCDR (SEQ ID NO:138), VH49BH (SEQ ID NO:139), VH72Bmax (SEQ ID NO:131), VH49B (SEQ ID NO:132), and VH49Bmax (SEQ ID NO:133).

In fact, the inventors surprisingly established that all these sequences show both a binding affinity comparable to their mouse counterpart, and a weaken immunogenicity.

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda.

The term "antibody", as used herein, refers to a monoclonal antibody per se.

Each heavy chain is comprised of a N-term heavy chain variable region (abbreviated herein as VH) and a heavy chain constant region. The heavy chain constant region is comprised of three domains (CH1, CH2, and CH3) for IgG, with a hinge domain between CH1 and CH2 domains.

Each light chain is comprised of a N-term light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known numbering systems including IMGT, Kabat and Chothia systems (IMGT, The International Immunogenetics Information System®, LEFRANC et al., *Nucleic Acids Research*, vol. 27, p: 209-212, 1999; KABAT, sequences of Proteins of Immunological Interest, 5$^{th}$ edition. U.S Department of Health and Human Services, Public Health Service, National Institutes of Health, NIH publication, No 91-3242, 991; CLOTHIA & LESK, *J Mol Biol.*, vol. 196(4), p: 901-917, 1987). The functional ability of the antibody to bind a particular antigen depends on the variable regions of each light/heavy chain pair, and is largely determined by the CDRs.

According to another preferred embodiment, the humanized light chain variable region (VL) polypeptide is the amino acid sequence SEQ ID NO:29.

According to another preferred embodiment, the humanized light chain variable region (VL) polypeptide is the amino acid sequence SEQ ID NO:7.

According to another preferred embodiment, the humanized heavy chain variable region (VH) polypeptide is the amino acid sequences SEQ ID NO:12.

According to still another preferred embodiment, the humanized heavy chain variable region (VH) polypeptide is the amino acid sequences SEQ ID NO:2.

The term "functional fragments" as used herein refers to antibody fragments, which bind specifically to the OAcGD2 ganglioside. Such fragments can be simply identified by the skilled person and comprise, as an example, ScFv fragment, $F_{ab}$ fragment (e.g., by papain digestion), $F_{ab}$' fragment (e.g., by pepsin digestion and partial reduction), $F(_{ab}')_2$ fragment (e.g., by pepsin digestion), $F_{acb}$ (e.g., by plasmin digestion), and also $F_v$ and $F_d$ (e.g., by pepsin digestion, partial reduction and re-aggregation) fragments are encompassed by the invention.

Such fragments can be produced by enzymatic cleavage, synthetic or recombinant technique using well known method in the art, such as described in STANWORTH et al (Handbook of Experimental Immunology, vol. 1, chapter 8, Blackwell Scientific Publications, 1978). Antibodies can also be produced in a variety of truncated forms using antibody genes in which one or more stop codons have been introduced upstream of the natural stop site. For example, a combination gene encoding a F$(_{ab}')_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

The expression "binding specifically to the O-acetylated GD2 ganglioside" refers to a binding affinity ($K_d$) of less than $5 \times 10^{-6}$ M at 25° C. for the O-acetylated GD2 ganglioside, preferably a $K_d$ of equal to or less than $5 \times 10^{-7}$ M, more preferably a $K_d$ of equal to or less than $1 \times 10^{-7}$ M or even $5 \times 10^{-8}$ M. Such affinity can be simply measured by techniques available in the art, e.g. Scatchard assay, competition ELISA, BIACORE assay or KINEXA assay.

The expression "binding specifically to the O-acetylated GD2 ganglioside" refers to a binding affinity ($K_d$) of more than $5 \times 10^{-5}$ M at 25° C. for GD2 ganglisoside, preferably a $K_d$ of more than $10^{-5}$ M for GD2 ganglioside.

Now, these fragments comprise at least the variable regions of the heavy and light chains described previously.

These fragments can be soluble, but also anchored within the cytoplasmic membrane, as a single-chain variable part of a chimeric antigen receptor (CAR).

The term "chimeric antigen receptors (CARs)," as used herein, refers to an artificial hybrid polypeptide comprising at least one antigen binding domain of an antibody and at least one effector cell signaling domain. Such CARs encompass engineered receptors that graft an artificial specificity onto a particular immune effector cell (e.g. T cells, NK cells and NKT cells). CARs may be employed to impart the specificity of a monoclonal antibody onto a T cell in a non-MHC-restricted manner, thus exploiting the antigen-binding properties of monoclonal antibodies. When expressed in T-cells, CARs recognize unprocessed antigens independently of their expression of major histocompatibility antigen which is unlike the physiologic T-Cell Receptors (TCR), thus bypassing two major mechanisms of tumor escape, the downregulation of HLA expression or proteosomal antigen processing. The binding of CARs to a specific antigen elicits an immune response.

In particular aspects, CARs comprise an ectodomain, a transmembrane domain and an endodomain. Now, the arrangement could be multimeric, such as a diabody or also multimers (e.g., the multi-chain chimeric antigen receptor described in International Patent application PCT WO 2016/016343).

The ectodomain corresponds to the antigen binding domain and to the spacer domain (stalk region). The antigen binding domain is preferably a single-chain variable fragment (scFv). Such scFv is a genetically engineered antibody fragment that usually consists of the heavy chain and light chain of an immunoglobulin, or parts thereof such as VH and VL, joined together by a flexible peptide linker as disclosed as an example in PLUCKTHUN (The Pharmacology of Monoclonal Antibodies, vol. 113, Rosenburg and Moore eds., Springer-Verlag, New York, p: 269-315, 1994). The flexible peptide linker can be a peptide of between 6 to 40 amino acid residues. The use of small amino acids such as alanine and glycine are of use in creating flexible linker. Exemplary flexible linkers include glycine polymers (G)n, glycine-serine polymers such as for example (GS)$_n$, GSGGS$_n$ (SEQ ID NO:113)n, GGGS$_n$ (SEQ ID NO:114)n and GGGGS$_n$ (SEQ ID NO:115)n, where n is an integer of at least one, glycine-alanine polymers or glycine-serine polymers, or other flexible linkers known in the art. As example of useful polymers, one can cite GGGGSGGGGSGGGGS ((G4S)3; SEQ ID NO:116), GST-SGSGKPGSGEGSTKG (CD19 linker; SEQ ID NO:117), GGSSRSSSSGGGGSGGGG (18mer; SEQ ID NO:118), GGGGSGGGGSGGGGSGGGGS ((G4S)4; SEQ ID NO:119), KESGSVSSEQLAQFRSLD (SEQ ID NO:120), EGKSSGSGSESKST (SEQ ID NO:121), GSAGSAAGSGEF (SEQ ID NO:122), GGGGGGGG (SEQ ID NO:123) or GGGGGG (SEQ ID NO:124). Finally, these scFv fragments can be obtained by methods well known to those skilled in the art, such as described by GILLILAND et al. (Tissue Antigens, vol. 47, p: 1-20, 1996). The term "stalk region" also called as "spacer or hinge domain" as used herein refers to any oligo- or polypeptide that functions to link the transmembrane domain to the ectodomain. In particular, stalk region are used to provide more flexibility and accessibility for the ectodomain. The spacer elements play a predominantly structural role in the CAR. The spacer physically separates the targeting moiety from the T-cell membrane. The optimum distance required is likely to be different for each antigen. To enable efficient target access, a spacer appears to be required if a CAR binds an epitope that lies close to the target cell membrane, or when an antigen is complex in size and glycosylation status. Human IgG-derived spacers (Hinge-CH2-CH3) are commonly used due to their stabilizing action on CAR expression but interactions between the Fc domain of the spacer and Fc gamma receptors (FcgRs) on myeloid cells can lead to activation-induced cell death of T-cells and limited persistence in-vivo. This can be overcome by deleting or modifying regions of the constant heavy (CH)2 domain that are essential for FcgR binding thereby improving CAR T-cell persistence and anti-tumour activity in-vivo in pre-clinical models. Other Hinge domains commonly used include those derived from CD28 or CD8 or other truncated fragments from Human IgG-derived spacers. In a preferred embodiment, the CAR comprises a stalk region between the ectodomain and the transmembrane domain. A stalk region may comprise up to 300 amino acids, preferably 10 to 100 amino acids and most preferably 25 to 50 amino acids. This stalk region may be derived from all or part of naturally occurring molecules, such as part of the extracellular region of CD8, CD4 or CD28, or from all or part of an antibody constant region. Alternatively, this stalk region may be a synthetic sequence.

The transmembrane domain is a membrane anchor domain and also a linker between the ectodomain and the endomain. This transmembrane domain may be a human IgG4Fc hinge region, a Fc region, a CD4 transmembrane domain, a T cell receptor transmembrane, or other transmembrane domains from other human transmembrane signaling proteins, such as CD16, TCR Zeta chain (CD3ζ), CD28 and CD8 and erythropoietin receptor, and mutants thereof. Preferably, this transmembrane domain is a T cell receptor transmembrane domain. Preferably, the T cell receptor transmembrane domain is issued from a transmembrane protein able to form a complex with the T cell receptor for antigen (TCR). Preferably, the T cell receptor transmembrane domain comprises part or all of one or more of TCR Zeta chain (CD3ζ), CD28, OX40/CD134, 4-1BB/CD137/TNFRSF9, FcεRIγ, ICOS/CD278, ILRB/CD122, IL-2RG/CD132, CD27, DAP10 and CD40.

The endodomain is an intracellular signaling domain, which is responsible for intracellular signaling following the binding of the ectodomain to the target antigen resulting in the activation of the immune cell. In other word, the intracellular signaling domain is responsible for the activation of at least one of the normal effector functions of the immune cell in which the chimeric receptor is expressed. The term "effector function" refers to a specialized function of a T cell, which can be a cytolytic activity or helper activity including the secretion of cytokines. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal.

Preferred examples of signal transducing domain for use in multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcɛRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4), an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, DAP-10, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, DAP-10, lymphocyte function-associated antigen-1 (LFA-1), CD2, CD7, LIGHT, NKG2C, B7-H3 and a ligand that specifically binds with CD83 and the like.

As used herein, the term "derivatives" refers to an amino acid sequence having a percentage of identity of at least 90%, preferably at least 95%, most preferably at least 98% (i.e. corresponding to about 10, 5 and 2 amino acids substitutions respectively) with an amino acid sequence selected in the group consisting of SEQ ID NO: 2, 3, 4, 5, 7, 8, 9, 10, 11, 12, 29, 40, 41, 42, 43, 44, 45, 46, 76 and 112, preferably of at least 99% (i.e. corresponding to about 1 amino acid substitution). Such derivatives can be simply identified by the skilled person in view of its personal knowledge and of the teaching of the present patent application. It will also be understood that natural amino acids may be replaced by chemically modified amino acids. Typically, such chemically modified amino acids increase the polypeptide half-life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the local homology algorithm developed by Smith and Waterman (Ad. App. Math., vol. 2, p: 482, 1981), by using the global homology algorithm developed by Neddleman and Wunsch (J. Mol. Biol., vol. 48, p: 443, 1970), by using the method of similarities developed by Pearson and Lipmolan (Proc. Natl. Acad. Sci. USA, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., Nucleic Acids Research, vol. 32, p: 1792, 2004). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

The antibody of the invention is produced recombinantly.

The antibody may or may not be glycosylated, though glycosylated antibodies are preferred. In a preferred embodiment, the antibody of the invention may be low fucose.

The antibody of the invention encompasses immunoconjugates.

As used herein, the term "immunoconjugate" refers to a conjugate molecule comprising at least one antibody, a functional fragment or derivative thereof, bound to a second molecule, preferably an immunomodulating agent, a cytotoxic agent or a radioisotope. Such immunoconjugate may be Antibody Drug Conjugates (ADCs), Immunocytokines (ICK) or Antibody Radio Conjugates (ARC). Now, this second molecule may be an antibody having a binding specificity for another antigen, the formed immunoconjugate being a bispecific antibody like a BiTEs (Bi-specific T-cell engagers). Said antibody or fragment thereof is complexed or covalently bound (e.g. fusion protein) to said second molecule. Preferably, said antibody or fragment thereof is bound to said second molecule by covalent linkage.

A second aspect of the invention is related to a pharmaceutical composition comprising at least one antibody as described herein, at least one functional fragment, or at least one derivative thereof, and a pharmaceutically acceptable carrier for use in therapy.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

Said composition may be in any pharmaceutical form suitable for administration to a patient, including but not limited to solutions, suspensions, lyophilized powders, capsule and tablets. Now, the route of administration of the composition of the invention is preferably parenteral; as used herein, the term "parenteral" includes intravenous, intramuscular, subcutaneous, intraperitoneal, rectal, vaginal, mucosal, intrathecal, intracranial, or intratumoral administration. Thus, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

Most preferably, the composition is in any pharmaceutical form suitable for intravenous administration to a patient.

The antibody, functional fragment or derivative of the invention may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Dispersions can also be prepared in glycerol, liquid polyethylene glycols, and mixtures thereof and in oils. Under ordinary conditions of storage and use, these preparations contain a preservative to prevent the growth of microorganisms.

The antibody, functional fragment or derivative of the invention can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The antibodies of the invention may also be modified, by pegylation as an example, so as to increase its biodisponibility.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, and half-life enhancing covalent and non-covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In another object, the composition as defined previously is for use in a method for preventing and/or treating cancer expressing the OAcGD2 ganglioside in a subject.

As used herein, the term "subject" denotes a mammal, such as a rodent, a feline, a canine or a primate, and most preferably a human.

In the context of the invention, the term "treating cancer expressing OAcGD2 ganglioside", as used herein, means the inhibition of the growth of such cancer cells. Preferably such treatment also leads to the regression of tumor growth or metastasis spread, i.e., the decrease in size of a measurable tumor. Most preferably, such treatment leads to the complete regression of the tumor.

Said cancer expressing the OAcGD2 ganglioside are selected in the group comprising neuroblastoma, glioma, retinoblastoma, Ewing's family of tumors, sarcoma (i.e. rhabdomyosarcoma, osteosarcoma, leiomyosarcoma, liposarcoma, and fibrosarcoma), small cell lung cancer, breast cancer, melanoma, metastatic renal carcinoma, head and neck cancer and hematological cancers (i.e. leukemia, Hodgkin lymphoma, non-Hodgkin lymphoma and myeloma).

The antibody of the invention is contained in said pharmaceutical composition in an amount effective to achieve the intended purpose, and in dosages suitable for the chosen route of administration.

An "effective amount" of the conjugate is an amount which is sufficient to induce the regression of tumor growth or metastasis spread. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

According to a preferred embodiment, the antibody, functional fragment or derivative thereof can be by administrated by injection at a dose comprised between 2 and 2,000 mg/m$^2$ of subject, preferably at a dose comprised between 5 and 1,000 mg/m$^2$, and most preferably at a dose comprised between 10 and 500 mg/m$^2$.

According to another preferred embodiment, the antibody, functional fragment or derivative thereof of the invention is in the form a chimeric antigen receptor (CAR). Thus, the amount of transduced cells (such as T cells, NKT cells or NK cells) administered should take into account the route of administration and should be such that a sufficient number of the transduced cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^4$ to about $1\times10^9$ transduced cells per m$^2$, even more desirably, from about $1\times10^6$ or $1\times10^7$ to about $5\times10^8$ transduced cells, although any suitable amount can be utilized either above, e.g., greater than $5\times10^8$ cells, or below, e.g., less than $1\times10^7$ cells. The dosing schedule can be based on well-established cell-based therapies (see, e.g., TOPALIAN and ROSENBERG, 1987; U.S. Pat. No. 4,690,915), or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on inter-individual differences in pharmacokinetics, drug disposition, and metabolism. One skilled in the art readily can make any necessary adjustments in accordance with the exigencies of the particular situation.

A third aspect of the present invention concerns a method for treating and/or preventing a cancer expressing the OAcGD2 ganglioside in a subject comprising the step of administrating to a subject in need thereof an effective amount of at least one antibody, functional fragment, or derivative thereof.

Preferably, a subject refers to a mammal and most preferably a human.

Said cancer expressing the OAcGD2 ganglioside are selected in the group comprising neuroblastoma, glioma, retinoblastoma, Ewing's family of tumors, sarcoma (i.e. rhabdomyosarcoma, osteosarcoma, leiomyosarcoma, liposarcoma, and fibrosarcoma), small cell lung cancer, breast cancer, melanoma, metastatic renal carcinoma, head and neck cancer and hematological cancers (i.e. leukemia, Hodgkin lymphoma, non-Hodgkin lymphoma and myeloma).

A forth aspect of the present invention concerns a method, preferably an in vitro method for diagnosing a cancer expressing the OAcGD2 ganglioside in a subject comprising the step of contacting a biological sample of said subject with at least one antibody as described herein, functional fragment, or derivative thereof, for determining the OAcGD2 ganglioside expression level in said biological sample, wherein a detectable OAcGD2 ganglioside expression level is indicative of such a cancer.

Preferably, said subject refers to a mammal and most preferably a human.

As used herein, a biological sample refers to a sample potentially comprising cancer cells such as a blood sample or a cancer biopsy.

Said cancer expressing the OAcGD2 ganglioside is selected in the group comprising neuroblastoma, glioma, retinoblastoma, Ewing's family of tumors, sarcoma (i.e. rhabdomyosarcoma, osteosarcoma, leiomyosarcoma, liposarcoma, and fibrosarcoma), small cell lung cancer, breast cancer, melanoma, metastatic renal carcinoma, head and neck cancer and hematological cancers (i.e. leukemia, Hodgkin lymphoma, non-Hodgkin lymphoma and myeloma).

In a preferred embodiment, the method of the invention further comprises the step of comparing said OAcGD2 ganglioside expression with a control.

As used herein said "control" refers to the OAcGD2 ganglioside expression level in a control sample corresponding to cells of a biological sample from a healthy subject.

In a fifth aspect, the present invention relates to a kit for diagnosing a cancer expressing the OAcGD2 ganglioside in a subject, which comprises at least one antibody, functional fragment or derivative as described previously and eventually means useful to the administration of said antibody, functional fragment or derivative thereof or said formulation to said subject.

As described previously, said antibody, functional fragment or derivative thereof of said kit may refer to an immunoconjugate suitable to be directly detected by means of imaging techniques for use in a in vivo method for diagnosing a cancer expressing the OAcGD2 ganglioside in a subject, for example an immunoconjugate comprising a fluorophore or a radioisotope, notably for a diagnostic by imaging and monitoring the responsiveness of a subject.

As used herein, the term "kit" refers to any delivery system for delivering materials. In the context of reaction assays, such delivery systems include systems that allow for the storage, transport, or delivery of reaction reagents and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The present kits can also include one or more reagents, buffers, hybridization media, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like. In one embodiment, the kit is made up of instructions for carrying out the method described herein. The instructions can be provided in any intelligible form through a tangible medium, such as printed on paper, computer readable media, or the like.

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

EXAMPLES

1) Humanization
1.1 1$^{st}$ Round:

The 8B6 sequence has been humanized using CDR-grafting method by using the most closed identified human germline. Then, the binding of the obtained humanized antibodies (OGD201) was tested by their incubation at different concentrations—i.e. 0.01 to 10 µg/ml—on IMR5 cells—i.e. expressing OAcGD2 at their surface—in PBS, 1% BSA for 45 minutes on ice. After incubation and washes, antibody binding was detected by incubation with a goat anti-mouse IgG coupled with FITC (Southern Biotech) for 30 min on ice. Finally, cell fluorescence was analyzed by flow cytometer.

Figure 2:
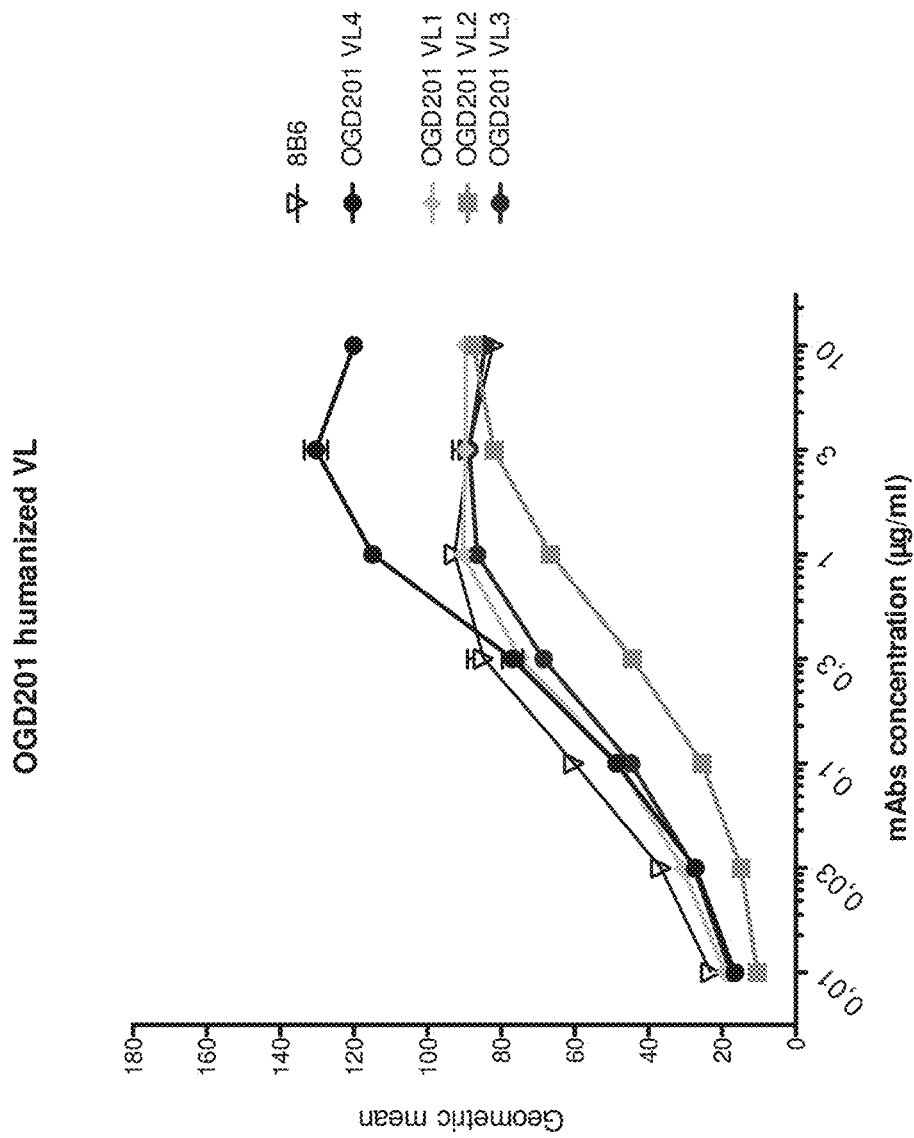
FIG. 2 presents the binding titration assays on IMR5 cells of VL humanized anti-OAcGD2 (8B6 VH) mAb as compared to the mouse antibody.

The results in relation with the only one functional germline are presented in table 1 and in FIGS. 1 and 2.

TABLE 1

| Name | Germline degree (%) | OAcGD2 binding | Amino-acid sequence |
|---|---|---|---|
| 8B6 VH (reference; SEQ ID NO: 1) | 74 | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 Consensus 1 VH (SEQ ID NO: 2) | At least 80 | + | E/QVQLVESGGG LVQ/KPGG/RSLRL SCA/TTSEFTFT DYYMTWVRQA PGKGLEWLGF IRNRANGYTT EYNPSVKGRF TISRDNS/AKS/NI/S LYLQMNSLR/KT/A EDTAVYYCAR VSNWAFDYWG QGTTLTVSS |
| OGD201 VH1 (SEQ ID NO: 3) | 87 | + | EVQLVESGGG LVQPGGSLRL SCATSEFTFT DYYMTWVRQA PGKGLEWLGF IRNRANGYTT EYNPSVKGRF TISRDNSKNS LYLQMNSLKT EDTAVYYCAR VSNWAFDYWG QGTLVTVSS |

TABLE 1-continued

| Name | Germline degree (%) | OAcGD2 binding | Amino-acid sequence |
|---|---|---|---|
| OGD201 VH2 (SEQ ID NO: 4) | 85 | + | EVQLVESGGG LVQPGRSLRL SCTTSEFTFT DYYMTWVRQA PGKGLEWLGF IRNRANGYTT EYNPSVKGRF TISRDNSKSI LYLQMNSLKT EDTAVYYCAR VSNWAFDYWG QGTLVTVSS |
| OGD201 VH3 (SEQ ID NO: 5) | 82 | + | QVQLVESGGG LVKPGGSLRL SCATSEFTFT DYYMTWVRQA PGKGLEWLGF IRNRANGYTT EYNPSVKGRF TISRDNAKNS LYLQMNSLRA EDTAVYYCAR VSNWAFDYWG QGTTLTVSS |
| 8B6 VL (reference; SEQ ID NO: 6) | 77 | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 Consensus 1 VL SEQ ID NO: 7 | At least 78 | + | D/EVV/QMTQSPL/AS/T LP/SV/AS/TL/P/VGD/Q/EQ/P/RA/VS/T I/LS/TCRSSQSLL KNNGNTFLHW YL/QQK/RPGQ/KS/APK/Q/R LLIYKVSNRL S/TGV/IPD/A/SRFSGS GSGTY/DFTLK/TI SR/SV/LE/QA/PEDL/V/FG/AV/T YF/YCSQSTHIP YTFGG/QGTKVE IK |
| OGD201 VL1 (SEQ ID NO: 8) | 87 | + | DVVMTQSPLS LPVTLGDPAS ISCRSSQSLL KNNGNTFLHW YQQRPGQSPR LLIYKVSNRL SGVPDRFSGS GSGTDFTLKI SRVEAEDVGV YFCSQSTHIP YTFGGGTKVE IK |
| OGD201 VL2 (SEQ ID NO: 9) | 78 | + | EVVMTQSPAT LSLSPGERAT LSCRSSQSLL KNNGNTFLHW YQQKPGQAPR LLIYKVSNRL TGIPARFSGS GSGTDFTLTI SSLQPEDFAV YFCSQSTHIP YTFGGGTKVE IK |
| OGD201 VL3 (SEQ ID NO: 10) | 84 | + | DVVMTQSPLS LPVTPGEPAS ISCRSSQSLL KNNGNTFLHW YLQKPGQSPQ LLIYKVSNRL SGVPDRFSGS GSGTDFTLKI SRVEAEDVGV YFCSQSTHIP YTFGQGTKVE IK |
| OGD201 VL4 (SEQ ID NO: 11) | 78 | + | DVQMTQSPSS LSASVGDRVT ITCRSSQSLL KNNGNTFLHW YQQKPGKAPK LLIYKVSNRL SGVPSRFSGS GSGTDFTLTI SSLQPEDVAT YYCSQSTHIP YTFGQGTKVE IK |

CDRs are represented in bold in the reference and consensus sequences, and mutated amino-acid mutated are highlighted in grey.

The FIG. 1 presents the binding titration assays on IMR5 cells of VH humanized anti-OAcGD2 mAb (OGD201 VH3 (SEQ ID NO:5), OGD201 VH2 (SEQ ID NO:4), and OGD201 VH1 (SEQ ID NO:3)) as compared to the mouse antibody (8B6).

The FIG. 2 presents the binding titration assays on IMR5 cells of VL humanized anti-OAcGD2 mAb (OGD201 VL1 (SEQ ID NO:8), OGD201 VL2 (SEQ ID NO:9), OGD201 VL3 (SEQ ID NO:10), and OGD201 VL4 (SEQ ID NO:11)) as compared to the mouse antibody (8B6).

Figure 3:
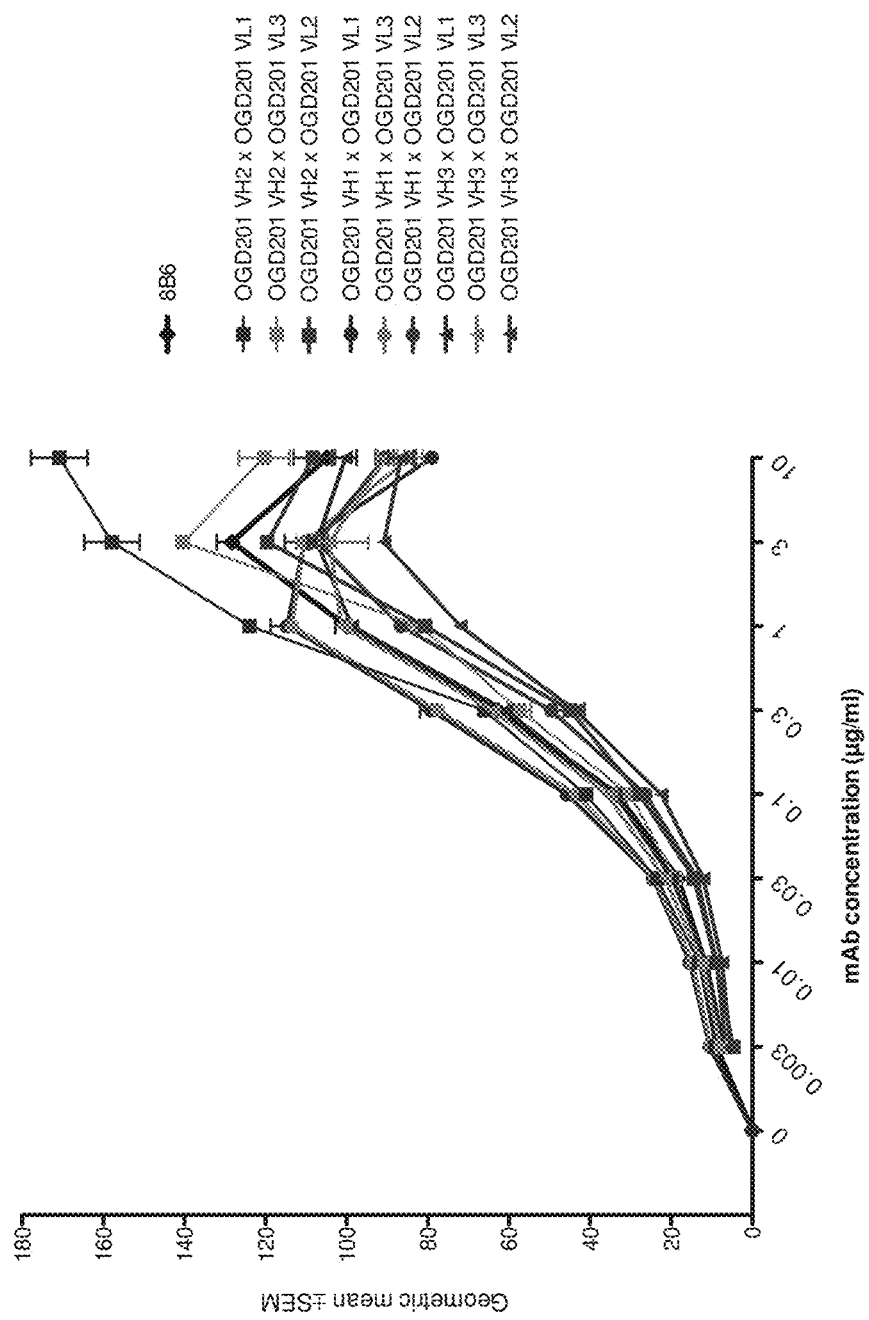
FIG. 3 presents the binding titration assays on IMR5 cells of VH-VL humanized anti-OAcGD2 mAb as compared to the mouse antibody.

The FIG. 3 presents the binding titration assays on IMR5 cells of VH-VL humanized anti-OAcGD2 mAbs as compared to the mouse antibody (8B6). These VH-VL humanized anti-OAcGD2 mAb combine the VH humanized anti-OAcGD2 mAb (OGD201 VH3 (SEQ ID NO:5), OGD201 VH2 (SEQ ID NO:4), or OGD201 VH1 (SEQ ID NO:3)) with the VL humanized anti-OAcGD2 mAb (OGD201 VL1 (SEQ ID NO:8), OGD201 VL2 (SEQ ID NO:9), OGD201 VL3 (SEQ ID NO:10), and OGD201 VL4 (SEQ ID NO:11)).

The results show that on the numerous tested human germline (data not shown), the inventors identified a first VH and VL consensus sequence having at least 83% and 84% of identity with a human germline. The obtained consensus sequence are nearly 10% and 7% more humanized than the original antibody respectively and have simultaneously a very good binding to OAcGD2 (See FIGS. 1, 2 and 3).

1.2 Optimization:

In the aim to increase the antibody humanization degree, the inventors initiate the testing of point mutations on the 8B6 sequences to select those not affecting the binding to OAcGD2. Then, the OAcGD2 binding of the obtained humanized antibodies (OGD201) was tested as described previously.

The results in relation with the tested point mutations are presented in table 2.

| Name | OAcGD2 binding | Amino-acid sequence |
|---|---|---|
| OGD201 VH4 (SEQ ID NO: 13) | + | EVKLLESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH5 (SEQ ID NO: 14) | + | EVKLVESGGG LVLPGDSLRL SCAASEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH6 (SEQ ID NO: 15) | + | EVKLVESGGG LVLPGDSLRL SCATSEFTFT DYYMTWVRQP PRKALEWVGF IRNRANGYTT EYNPSVKGRF TISRDNSQSI LYLQMNTLRT EDSATYYCAR VSNWAFDYWG QGTTLTVSS |
| OGD201 VH7 (SEQ ID NO: 16) | + | EVKLVESGGG LVLPGDSLRL SCATSEFTFT DYYMTWVRQP PRKALEWLSF IRNRANGYTT EYNPSVKGRF TISRDNSQSI LYLQMNTLRT EDSATYYCAR VSNWAFDYWG QGTTLTVSS |
| OGD201 VH8 (SEQ ID NO: 17) | - | EVKLVESGGG LVLPGDSLRL SCATSEFTFT DYYMTWVRQP PRKALEWLGF IRNRAQGYTT EYNPSVKGRF TISRDNSQSI LYLQMNTLRT EDSATYYCAR VSNWAFDYWG QGTTLTVSS |
| OGD201 VH9 (SEQ ID NO: 18) | + | EVKLVESGGG LVLPGDSLRL SCATSEFTFT DYYMTWVRQP PRKALEWLGF IRNRANAYTT EYNPSVKGRF TISRDNSQSI LYLQMNTLRT EDSATYYCAR VSNWAFDYWG QGTTLTVSS |
| OGD201 VH10 (SEQ ID NO: 19) | + | EVKLVESGGG LVLPGDSLRL SCATSEFTFT DYYMTWVRQP PRKALEWLGF IRNRANGYTT EYAPSVKGRF TISRDNSQSI LYLQMNTLRT EDSATYYCAR VSNWAFDYWG QGTTLTVSS |
| OGD201 VH11 (SEQ ID NO: 20) | + | EVKLVESGGG LVLPGDSLRL SCATSEFTFT DYYMTWVRQP PRKALEWLGF IRNRANGYTT EYNASVKGRF TISRDNSQSI LYLQMNTLRT EDSATYYCAR VSNWAFDYWG QGTTLTVSS |
| OGD201 VH12 (SEQ ID NO: 21) | - | EVKLVESGGG LVLPGDSLRL SCATSEFTFT DYYMTWVRQP PRKALEWLGF IRNRANGYTT EYNPSVKGRF TISRDDSQSI LYLQMNTLRT EDSATYYCAR VSNWAFDYWG QGTTLTVSS |
| OGD201 VH13 (SEQ ID NO: 22) | + | EVKLVESGGG LVLPGDSLRL SCATSEFTFT DYYMTWVRQP PRKALEWLGF IRNRANGYTT EYNPSVKGRF TISRDNSQST LYLQMNTLRT EDSATYYCAR VSNWAFDYWG QGTTLTVSS |
| OGD201 VH14 (SEQ ID NO: 23) | + | EVKLVESGGG LVLPGDSLRL SCATSEFTFT DYYMTWVRQP PRKALEWLGF IRNRANGYTT EYNPSVKGRF TISRDNSQSI TYLQMNTLRT EDSATYYCAR VSNWAFDYWG QGTTLTVSS |
| OGD201 VH15 (SEQ ID NO: 24) | + | EVKLVESGGG LVLPGDSLRL SCATSEFTFT DYYMTWVRQP PRKALEWLGF IRNRANGYTT EYNPSVKGRF TISRDNSQSI LYLQMNTLQT EDSATYYCAR VSNWAFDYWG QGTTLTVSS |
| OGD201 VH16 (SEQ ID NO: 25) | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH17 (SEQ ID NO: 26) | - | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNPAFDYWG QGTTLTVSS |
| OGD201 VH18 (SEQ ID NO: 27) | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTLLTVSS |
| OGD201 VH19 (SEQ ID NO: 28) | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTVTVSS |
| OGD201 Consensus 2 VH (SEQ ID NO: 12) | | E/QVQLV/LESGGG LVQ/KPGG/RSLRL SCA/TT/ASEFTFT DYYMTWVRQA PGKGLEWL/VG/SF IRNRANG/AYTT EYN/AP/ASVKGRF TISRDN/AKS/NI/S/T L/TYLQMNSLR/K/QT/A EDTAV/IYYCAR VSNWAFDYWG QGTT/LL/VTVSS |

-continued

| Name | OAcGD2 binding | Amino-acid sequence |
|---|---|---|
| OGD201 VL5 (SEQ ID NO: 30) | + | DVVMTQTPLS LPVSLGDQAS ISCRSSQSLV KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL6 (SEQ ID NO: 31) | − | DVVMTQTPLS LPVSLGDQAS ISCRSSQSLL HNNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL7 (SEQ ID NO: 32) | + | DVVMTQTPLS LPVSLGDQAS ISCRSSQSLL KNQGNTFLHW YLQKSGQSPK LLIYKVSNRL SGVPDRFSGS GSGTYFTLKI SRVEAEDLGV YFCSQSTHIP YTFGGGTKLE IK |
| OGD201 VL8 (SEQ ID NO: 33) | + | DVVMTQTPLS LPVSLGDQAS ISCRSSQSLL KNNANTFLHW YLQKSGQSPK LLIYKVSNRL SGVPDRFSGS GSGTYFTLKI SRVEAEDLGV YFCSQSTHIP YTFGGGTKLE IK |
| OGD201 VL9 (SEQ ID NO: 34) | + | DVVMTQTPLS LPVSLGDQAS ISCRSSQSLL KNNGNTYLHW YLQKSGQSPK LLIYKVSNRL SGVPDRFSGS GSGTYFTLKI SRVEAEDLGV YFCSQSTHIP YTFGGGTKLE IK |
| OGD201 VL10 (SEQ ID NO: 35) | + | DVVMTQTPLS LPVSLGDQAS ISCRSSQSLL KNNGNTFLHW RLQKSGQSPK LLIYKVSNRL SGVPDRFSGS GSGTYFTLKI SRVEAEDLGV YFCSQSTHIP YTFGGGTKLE IK |
| OGD201 VL11 (SEQ ID NO: 36) | + | DVVMTQTPLS LPVSLGDQAS ISCRSSQSLL KNNGNTFLHW YLQKSGQSPK RLIYKVSNRL SGVPDRFSGS GSGTYFTLKI SRVEAEDLGV YFCSQSTHIP YTFGGGTKLE IK |
| OGD201 VL12 (SEQ ID NO: 37) | + | DVVMTQTPLS LPVSLGDQAS ISCRSSQSLL KNNGNTFLHW YLQKSGQSPK VLIYKVSNRL SGVPDRFSGS GSGTYFTLKI SRVEAEDLGV YFCSQSTHIP YTFGGGTKLE IK |
| OGD201 VL13 (SEQ ID NO: 38) | + | DVVMTQTPLS LPVSLGDQAS ISCRSSQSLL KNNGNTFLHW YLQKSGQSPK LLIYKVSNRL SGVPDRFSGS GSGTYFTLKI NRVEAEDLGV YFCSQSTHIP YTFGGGTKLE IK |
| OGD201 VL14 (SEQ ID NO: 39) | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YYCSQSTHIP YTFGGGTKLE IK |
| OGD201 Consensus 2 VL (SEQ ID NO: 29) | | D/EVVMTQSPL/AS/T LP/SV/L/AS/TL/P/VGD/Q/EQ/P/RA/VS/T I/LS/TCRSSQSLL/V KNN/QG/ANTF/YLHW Y/FL/QQK/RPGQ/KS/APK/Q/R L/R/VLIYKVSNRL S/TGV/IPD/A/SRFSGS GSGTY/DFTLK/TI S/NR/SV/LE/QA/PEDL/V/FG/AV/T YF/YCSQSTHIP YTFGG/QGTKV/E IK |

CDRs are represented in bold in the consensus sequences, and mutated amino-acid mutated are highlighted in grey.

The inventors identified new positions which can be mutated/humanized without affecting the OAcGD2 binding. On the basis of these results, the inventors established a new consensus sequences enabling the obtaining of more humanized antibodies degree (consensus sequences 2).

1.3 Humanization 2$^{nd}$ Round:

On the basis of the optimization step done previously and of the corresponding consensus sequences, the inventors designed new humanized VH and VL sequences that were tested for their binding to OAcGD2.

| Name | Germline degree (%) | OAcGD2 binding | Amino-acid sequence |
|---|---|---|---|
| 8B6 VH (reference; SEQ ID NO: 1) | 74 | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |

| Name | Germline degree (%) | OAcGD2 binding | Amino-acid sequence |
| --- | --- | --- | --- |
| OGD201 Consensus 2 VH (SEQ ID NO: 12) | – | | E/QVQLV/LESGGG LVQ/KPGG/RSLRL SCA/TT/ASEFTFT DYYMTWVRQA PGKGLEWL/VG/SF IRNRANG/AYTT EYN/AP/ASVKGRF TISRDNS/AKS/NI/S/T L/TYLQMNSLR/K/QT/A EDTAV/IYYCAR VSNWAFDYWG QGTT/LL/VTVSS |
| OGD201 VH19 (SEQ ID NO: 40) | 91 | | EVQLVESGGG LVQPGGSLRL SCAASEFTFT DYYMTWVRQA PGKGLEWVGF IRNRANAYTT EYAASVKGRF TISRDNSKNS LYLQMNSLKT EDTAVYYCAR VSNWAFDYWG QGTLVTVSS |
| OGD201 VH20 (SEQ ID NO: 41) | 90 | | EVQLVESGGG LVQPGGSLRL SCAASEFTFT DYYMTWVRQA PGKGLEWLGF IRNRANAYTT EYAASVKGRF TISRDNSKNS LYLQMNSLKT EDTAVYYCAR VSNWAFDYWG QGTLVTVSS |
| OGD201 VH21 (SEQ ID NO: 42) | 87 | | EVQLVESGGG LVQPGRSLRL SCTASEFTFT DYYMTWVRQA PGKGLEWLGF IRNRANAYTT EYAASVKGRF TISRDNSKSI LYLQMNSLKT EDTAVYYCAR VSNWAFDYWG QGTLVTVSS |
| OGD201 VH72BCDR (SEQ ID NO: 136) | 88 | + | EVQLVESGGG LVQPGGSLRL SCAASEFTFT DYYMTWVRQA PGKGLEWLGF IRNRANGYTT EYNPSVKGRF TISRDNSKNS LYLQMNLKT EDTAVYYCAR VSNWAFDYWG QGTLVTVSS |
| OGD201 72BH (SEQ ID NO: 137) | 91 | + | EVQLVESGGG LVQPGGSLRL SCAASEFTFT DYYMTWVRQA PGKGLEWLGF IRNRANGYTT EYNPSVKGRF TISRDNSKNS LYLQMNLKT EDTAVYYCAR VSNWAFDYWG QGTLVTVSS |
| OGD201 VH49BCDR (SEQ ID NO: 138) | 88 | + | EVQLVESGGG LVQPGGSLRL SCAASEFTFT DYYMTWVRQA PGKGLEWLGF IRNRANGYTT EYNPSVKGRF TISRDNSKNS LYLQMNLKT EDTAVYYCAR VSNWAFDYWG QGTLVTVSS |
| OGD201 VH49BH (SEQ ID NO: 139) | 86 | + | EVQLVESGGG LVQPGGSLRL SCAASEFTFT DYYMTWVRQA PGKGLEWLGF IRNRANGYTT EYNPSVKGRF TISRDNSKNS LYLQMNLKT EDTAVYYCAR VSNWAFDYWG QGTLVTVSS |
| 8B6 VL (reference; SEQ ID NO: 6) | 77 | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 Consensus 2 VL (SEQ ID NO: 29) | – | | D/EVVMTQSPL/AS/T LP/SV/L/AS/TL/P/VGD/Q/EQ/P/RA/VS/T I/LS/TCRSSQSLL/V KNN/QG/ANTF/YLHW Y/FL/QQK/RPGQ/KS/APK/Q/R L/R/VLIYKVSNRL S/TGV/IPD/A/SRFSGS GSGTY/DFTLK/TI S/NR/SV/LE/QA/PEDL/V/FG/AV/T YF/XCSQSTHIP YTFGG/XGTKX/E IK |
| OGD201 VL15 SEQ ID NO: 43) | 90 | | DVVMTQSPLS LPVTLGQPAS ISCRSSQSLV KNQANTYLHW FQQRPGQSPR LLIYKVSNRL SGVPDRFSGS GSGTDFTLKI SRVEAEDVGV YXCSQSTHIP YTFGGGTKVE IK |
| OGD201 VL16 SEQ ID NO: 44) | 74 | | EVVMTQSPAT LSLTPGQPAT LSCRSSQSLV KNQANTYLHW FQQRPGQSPR LLIYKVSNRL TGIPARFSGS GSGTDFTLTI SSLQPEDVAV YXCSQSTHIP YTFGGGTKVE IK |

-continued

| Name | Germline degree (%) | OAcGD2 binding | Amino-acid sequence |
|---|---|---|---|
| OGD201 VL17 (SEQ ID NO: 45) | 79 | | EVVMTQSPAT LSLSPGERAT LSCRSSQSLV KNQANTYLHW YQQKPGQAPR LLIYKVSNRL TGIPARFSGS GSGTDFTLTI SSLQAEDRAV YYCSQSTHIP YTFGGGTKVE IK |
| OGD201 VL18 (SEQ ID NO: 46) | 77 | | EVVMTQSPAT LSLTPGERAT LSCRSSQSLV KNQANTYLHW RQQRPGQAPR LLIYKVSNRL TGIPARFSGS GSGTDFTLTI SSLQPEDRAV YYCSQSTHIP YTFGGGTKVE IK |
| OGD201 VL28BH (SEQ ID NO: 140) | 85 | + | DVVMTQSPLS LPVSPGEPAS ISCRSSQSLL KNNANTFLHW YLQKPGQSPQ LLIYKVSNRA SGVPDRFSGS GSGTDFTLKI SRVEAEDVGV YYCSQSTHIP YTFGGGTKVE IK |

CDRs are represented in bold and mutated amino-acid mutated are highlighted in grey.

Then, the binding of the obtained humanized antibodies is tested by their incubation at different concentrations—i.e. 0.01 to 10 μg/ml—on IMR5 cells—i.e. expressing OAcGD2 at their surface—in PBS, 1% BSA for 45 minutes on ice. After incubation and washes, antibody binding is detected by incubation with a goat anti-mouse IgG coupled with FITC (Southern Biotech) for 30 min on ice. Finally, cell fluorescence is analyzed by flow cytometer.

1.4 Optimization:

So as to increase again the antibody humanization degree, the inventors initiate a new round of point mutations in the CDR this time so as to select those not affecting the binding to OAcGD2. Then, the OAcGD2 binding of the obtained antibodies is tested as described previously.

The tested point mutations are presented in table 4.

TABLE 4

| Name | OAcGD2 binding | Amino-acid sequence |
|---|---|---|
| OGD201 VH22 (SEQ id no 47) | + | EVKLVESGGG LVLPGDSLRL SCATSGFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH23 (SEQ id no 48) | + | EVKLVESGGG LVLPGDSLRL SCATSEFTST DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH24 (SEQ id no 49) | + | EVKLVESGGG LVLPGDSLRL SCATSEFTGT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH25 (SEQ id no 50) | + | EVKLVESGGG LVLPGDSLRL SCATSEFTFT DHYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH26 (SEQ id no 51) | - | EVKLVESGGG LVLPGDSLRL SCATSEFTFT DYAMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH27 (SEQ id no 52) | - | EVKLVESGGG LVLPGDSLRL SCATSEFTFT DYYMDWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH28 (SEQ id no 53) | + | EVKLVESGGG LVLPGDSLRL SCATSEFTFT DYYMSWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH29 (SEQ id no 54) | | EVKLVESGGG LVLPGDSLRL SCATSEFTFT DYYMHWVRQP PRKALEWLGF IRNRANGYTT EYNPSVKGRF TISRDNSQSI LYLQMNTLRT EDSATYYCAR VSNWAFDYWG QGTTLTVSS |
| OGD201 VH30 (SEQ id no 55) | | EVKLVESGGG LVLPGDSLRL SCATSEFTFT DYYMNWVRQP PRKALEWLGF IRNRANGYTT EYNPSVKGRF TISRDNSQSI LYLQMNTLRT EDSATYYCAR VSNWAFDYWG QGTTLTVSS |

TABLE 4-continued

| Name | OAcGD2 binding | Amino-acid sequence |
|---|---|---|
| OGD201 VH51 (SEQ id no 126) | + | EVKLVESGGG LVLPGDSLRL SCATSEFTFT DYYMTWIRQP PRKALEWLGF IRNRANGYTT EYNPSVKGRF TISRDNSQSI LYLQMNTLRT EDSATYYCAR VSNWAFDYWG QGTTLTVSS |
| OGD201 VH31 (SEQ id no 56) | − | EVKLVESGGG LVLPGDSLRL SCATSEFTFT DYYMTWVRQP PRKALEWLGR IRNRANGYTT EYNPSVKGRF TISRDNSQSI LYLQMNTLRT EDSATYYCAR VSNWAFDYWG QGTTLTVSS |
| OGD201 VH32 (SEQ id no 57) | + | EVKLVESGGG LVLPGDSLRL SCATSEFTFT DYYMTWVRQP PRKALEWLGY IRNRANGYTT EYNPSVKGRF TISRDNSQSI LYLQMNTLRT EDSATYYCAR VSNWAFDYWG QGTTLTVSS |
| OGD201 VH33 (SEQ id no 58) | + | EVKLVESGGG LVLPGDSLRL SCATSEFTFT DYYMTWVRQP PRKALEWLGF TRNRANGYTT EYNPSVKGRF TISRDNSQSI LYLQMNTLRT EDSATYYCAR VSNWAFDYWG QGTTLTVSS |
| OGD201 VH34 (SEQ id no 59) | − | EVKLVESGGG LVLPGDSLRL SCATSEFTFT DYYMTWVRQP PRKALEWLGF IRSRANGYTT EYNPSVKGRF TISRDNSQSI LYLQMNTLRT EDSATYYCAR VSNWAFDYWG QGTTLTVSS |
| OGD201 VH35 (SEQ id no 60) | + | EVKLVESGGG LVLPGDSLRL SCATSEFTFT DYYMTWVRQP PRKALEWLGF IRNKANGYTT EYNPSVKGRF TISRDNSQSI LYLQMNTLRT EDSATYYCAR VSNWAFDYWG QGTTLTVSS |
| OGD201 VH36 (SEQ id no 61) | + | EVKLVESGGG LVLPGDSLRL SCATSEFTFT DYYMTWVRQP PRKALEWLGF IRNSANGYTT EYNPSVKGRF TISRDNSQSI LYLQMNTLRT EDSATYYCAR VSNWAFDYWG QGTTLTVSS |
| OGD201 VH37 (SEQ id no 62) | + | EVKLVESGGG LVLPGDSLRL SCATSEFTFT DYYMTWVRQP PRKALEWLGF IRNRSNGYTT EYNPSVKGRF TISRDNSQSI LYLQMNTLRT EDSATYYCAR VSNWAFDYWG QGTTLTVSS |
| OGD201 VH38 (SEQ id no 63) | − | EVKLVESGGG LVLPGDSLRL SCATSEFTFT DYYMTWVRQP PRKALEWLGF IRNRAYGYTT EYNPSVKGRF TISRDNSQSI LYLQMNTLRT EDSATYYCAR VSNWAFDYWG QGTTLTVSS |
| OGD201 VH52 (SEQ id no 127) | − | EVKLVESGGG LVLPGDSLRL SCATSEFTFT DYYMTWVRQP PRKALEWLGF IRNRASGYTT EYNPSVKGRF TISRDNSQSI LYLQMNTLRT EDSATYYCAR VSNWAFDYWG QGTTLTVSS |
| OGD201 VH39 (SEQ id no 64) | + | EVKLVESGGG LVLPGDSLRL SCATSEFTFT DYYMTWVRQP PRKALEWLGF IRNRANSYTT EYNPSVKGRF TISRDNSQSI LYLQMNTLRT EDSATYYCAR VSNWAFDYWG QGTTLTVSS |
| OGD201 VH40 (SEQ id no 65) | − | EVKLVESGGG LVLPGDSLRL SCATSEFTFT DYYMTWVRQP PRKALEWLGF IRNRANGSTT EYNPSVKGRF TISRDNSQSI LYLQMNTLRT EDSATYYCAR VSNWAFDYWG QGTTLTVSS |
| OGD201 VH41 (SEQ id no 66) | + | EVKLVESGGG LVLPGDSLRL SCATSEFTFT DYYMTWVRQP PRKALEWLGF IRNRANGGTT EYNPSVKGRF TISRDNSQSI LYLQMNTLRT EDSATYYCAR VSNWAFDYWG QGTTLTVSS |
| OGD201 VH53 (SEQ id no 128) | + | EVKLVESGGG LVLPGDSLRL SCATSEFTFT DYYMTWVRQP PRKALEWLGF IRNRANGYTI EYNPSVKGRF TISRDNSQSI LYLQMNTLRT EDSATYYCAR VSNWAFDYWG QGTTLTVSS |
| OGD201 VH42 (SEQ id no 67) | + | EVKLVESGGG LVLPGDSLRL SCATSEFTFT DYYMTWVRQP PRKALEWLGF IRNRANGYTT YNPSVKGRF TISRDNSQSI LYLQMNTLRT EDSATYYCAR VSNWAFDY**WG QGTTLTVSS |
| OGD201 VH54 (SEQ id no 129) | + | EVKLVESGGG LVLPGDSLRL SCATSEFTFT DYYMTWVRQP PRKALEWLGF IRNRANGYTT EYNDSVKGRF TISRDNSQSI LYLQMNTLRT EDSATYYCAR VSNWAFDY**WG QGTTLTVSS |
| OGD201 VH43 (SEQ id no 68) | + | EVKLVESGGG LVLPGDSLRL SCATSEFTFT DYYMTWVRQP PRKALEWLGF IRNRANGYTT EYNPSVKGRF TISRDGSQSI LYLQMNTLRT EDSATYYCAR VSNWAFDYWG QGTTLTVSS |

TABLE 4-continued

| Name | OAcGD2 binding | Amino-acid sequence |
|---|---|---|
| OGD201 VH44 (SEQ id no 69) | | EVKLVESGGG LVLPGDSLRL SCATSEFTFT DYYMTWVRQP PRKALEWLGF IRNRANGYTT EYNPSVKGRF TISRDNAQSI LYLQMNTLRT EDSATYYCAR VSNWAFDYWG QGTTLTVSS |
| OGD201 VH45 (SEQ id no 70) | + | EVKLVESGGG LVLPGDSLRL SCATSEFTFT DYYMTWVRQP PRKALEWLGF IRNRANGYTT EYNPSVKGRF TISRDNSQSI AYLQMNTLRT EDSATYYCAR VSNWAFDYWG QGTTLTVSS |
| OGD201 VH46 (SEQ id no 71) | | EVKLVESGGG LVLPGDSLRL SCATSEFTFT DYYMTWVRQP PRKALEWLGF IRNRANGYTT EYNPSVKGRF TISRDNSQSI LYLQMNTLRA EDSATYYCAR VSNWAFDYWG QGTTLTVSS |
| OGD201 VH47 (SEQ id no 72) | | EVKLVESGGG LVLPGDSLRL SCATSEFTFT DYYMTWVRQP PRKALEWLGF IRNRANGYTT EYNPSVKGRF TISRDNSQSI LYLQMNTLRT EDSALYYCAR VSNWAFDYWG QGTTLTVSS |
| OGD201 VH48 (SEQ id no 73) | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCTR VSNWAFDYWG QGTTLTVSS |
| OGD201 VH49 (SEQ id no 74) | - | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNYAFDYWG QGTTLTVSS |
| OGD201 VH50 (SEQ id no 75) | - | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWYFDYWG QGTTLTVSS |
| OGD201 Consensus 3 VH (SEQ id no 76) | | E/QVQLV/LESGGG LVQ/KPGG/RSLRL SCA/TT/ASEGFTFT/S/G DY/HYMT/H/N/∗SWV/IRQA PRKGLEWL/VG/SF/Y I/TRNR/K/SA/SNG/A/SY /GT/IT/I E/YYN/AP/A/DSVKGRF TISRDN/GS/AKS/NI/S/T L/T/AYLQMNTLR/QT/A EDTAV/I/LYYCA/TR VSNW/YA/YFDY**WG QGTT/LL/VTVSS |
| OGD201 VL54 (SEQ id no 130) | + | DIVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL19 (SEQ id no 77) | | DVVMTQTPLS LPVSLGDQAS ISCRASQSLL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL20 (SEQ id no 78) | | DVVMTQTPLS LPVSLGDQAS ISCRSSQSVL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL21 (SEQ id no 79) | + | DVVMTQTPLS LPVSLGDQAS ISCRSSQSLL KSNGNTFLHW YLQKSGQSPK LLIYKVSNRL SGVPDRFSGS GSGTYFTLKI SRVEAEDLGV YFCSQSTHIP YTFGGGTKLE IK |
| OGD201 VL22 (SEQ id no 80) | - | DVVMTQTPLS LPVSLGDQAS ISCRSSQSLL KNDGNTFLHW YLQKSGQSPK LLIYKVSNRL SGVPDRFSGS GSGTYFTLKI SRVEAEDLGV YFCSQSTHIP YTFGGGTKLE IK |
| OGD201 VL23 (SEQ id no 81) | | DVVMTQTPLS LPVSLGDQAS ISCRSSQSLL KNNSNTFLHW YLQKSGQSPK LLIYKVSNRL SGVPDRFSGS GSGTYFTLKI SRVEAEDLGV YFCSQSTHIP YTFGGGTKLE IK |
| OGD201 VL24 (SEQ id no 82) | + | DVVMTQTPLS LPVSLGDQAS ISCRSSQSLL KNNGYTFLHW YLQKSGQSPK LLIYKVSNRL SGVPDRFSGS GSGTYFTLKI SRVEAEDLGV YFCSQSTHIP YTFGGGTKLE IK |

TABLE 4-continued

| Name | OAcGD2 binding | Amino-acid sequence |
|---|---|---|
| OGD201 VL25 (SEQ id no 83) | | DVVMTQTPLS LPVSLGDQAS ISCRSSQSLL KNNGSTFLHW YLQKSGQSPK LLIYKVSNRL SGVPDRFSGS GSGTYFTLKI SRVEAEDLGV YFCSQSTHIP YTFGGGTKLE IK |
| OGD201 VL26 (SEQ id no 84) | + | DVVMTQTPLS LPVSLGDQAS ISCRSSQSLL KNNGNNFLHW YLQKSGQSPK LLIYKVSNRL SGVPDRFSGS GSGTYFTLKI SRVEAEDLGV YFCSQSTHIP YTFGGGTKLE IK |
| OGD201 VL27 (SEQ id no 85) | | DVVMTQTPLS LPVSLGDQAS ISCRSSQSLL KNNGNSFLHW YLQKSGQSPK LLIYKVSNRL SGVPDRFSGS GSGTYFTLKI SRVEAEDLGV YFCSQSTHIP YTFGGGTKLE IK |
| OGD201 VL28 (SEQ id no 86) | + | DVVMTQTPLS LPVSLGDQAS ISCRSSQSLL KNNGNTFLNW YLQKSGQSPK LLIYKVSNRL SGVPDRFSGS GSGTYFTLKI SRVEAEDLGV YFCSQSTHIP YTFGGGTKLE IK |
| OGD201 VL29 (SEQ id o 87) | | DVVMTQTPLS LPVSLGDQAS ISCRSSQSLL KNNGNTFLSW YLQKSGQSPK LLIYKVSNRL SGVPDRFSGS GSGTYFTLKI SRVEAEDLGV YFCSQSTHIP YTFGGGTKLE IK |
| OGD201 VL30 (SEQ id o 88) | | DVVMTQTPLS LPVSLGDQAS ISCRSSQSLL KNNGNTFLAW YLQKSGQSPK LLIYKVSNRL SGVPDRFSGS GSGTYFTLKI SRVEAEDLGV YFCSQSTHIP YTFGGGTKLE IK |
| OGD201 VL31 (SEQ id o 89) | − | DVVMTQTPLS LPVSLGDQAS ISCRSSQSLL KNNGNTFLDW YLQKSGQSPK LLIYKVSNRL SGVPDRFSGS GSGTYFTLKI SRVEAEDLGV YFCSQSTHIP YTFGGGTKLE IK |
| OGD201 VL32 (SEQ id o 90) | | DVVMTQTPLS LPVSLGDQAS ISCRSSQSLL KNNGNTFLYW YLQKSGQSPK LLIYKVSNRL SGVPDRFSGS GSGTYFTLKI SRVEAEDLGV YFCSQSTHIP YTFGGGTKLE IK |
| OGD201 VL33 (SEQ id o 91) | | DVVMTQTPLS LPVSLGDQAS ISCRSSQSLL KNNGNTFLGW YLQKSGQSPK LLIYKVSNRL SGVPDRFSGS GSGTYFTLKI SRVEAEDLGV YFCSQSTHIP YTFGGGTKLE IK |
| OGD201 VL34 (SEQ id o 92) | | DVVMTQTPLS LPVSLGDQAS ISCRSSQSLL KNNGNTFLHW YLQKSGQAPK LLIYKVSNRL SGVPDRFSGS GSGTYFTLKI SRVEAEDLGV YFC`FGGGTKLE IK |
| OGD201 VL35 (SEQ id o 93) | | DVVMTQTPLS LPVSLGDQAS ISCRSSQSLL KNNGNTFLHW YLQKSGQVPK LLIYKVSNRL SGVPDRFSGS GSGTYFTLKI SRVEAEDLGV YFCSQSTHIP YTFGGGTKLE IK |
| OGD201 VL36 (SEQ id no 94) | | DVVMTQTPLS LPVSLGDQAS ISCRSSQSLL KNNGNTFLHW YLQKSGQSPK LLIYGVSNRL SGVPDRFSGS GSGTYFTLKI SRVEAEDLGV YFCSQSTHIP YTFGGGTKLE IK |
| OGD201 VL37 (SEQ id no 95) | + | DVVMTQTPLS LPVSLGDQAS ISCRSSQSLL KNNGNTFLHW YLQKSGQSPK LLIYLVSNRL SGVPDRFSGS GSGTYFTLKI SRVEAEDLGV YFCSQSTHIP YTFGGGTKLE IK |
| OGD201 VL38 (SEQ id no 96) | | DVVMTQTPLS LPVSLGDQAS ISCRSSQSLL KNNGNTFLHW YLQKSGQSPK LLIYKASNRL SGVPDRFSGS GSGTYFTLKI SRVEAEDLGV YFCSQSTHIP YTFGGGTKLE IK |
| OGD201 VL39 (SEQ id no 97) | + | DVVMTQTPLS LPVSLGDQAS ISCRSSQSLL KNNGNTFLHW YLQKSGQSPK LLIYKGSNRL SGVPDRFSGS GSGTYFTLKI SRVEAEDLGV YFCSQSTHIP YTFGGGTKLE IK |
| OGD201 VL40 (SEQ id no 98) | | DVVMTQTPLS LPVSLGDQAS ISCRSSQSLL KNNGNTFLHW YLQKSGQSPK LLIYKVSTRL SGVPDRFSGS GSGTYFTLKI SRVEAEDLGV YFCSQSTHIP YTFGGGTKLE IK |

TABLE 4-continued

| Name | OAcGD2 binding | Amino-acid sequence |
|---|---|---|
| OGD201 VL41 (SEQ id no 99) | + | DVVMTQTPLS LPVSLGDQAS ISCRSSQSLL KNNGNTFLHW YLQKSGQSPK LLIYKVSNRA SGVPDRFSGS GSGTYFTLKI SRVEAEDLGV YFCSQSTHIP YTFGGGTKLE IK |
| OGD201 VL42 (SEQ id no 100) | + | DVVMTQTPLS LPVSLGDQAS ISCRSSQSLL KNNGNTFLHW YLQKSGQSPK LLIYKVSNRD SGVPDRFSGS GSGTYFTLKI SRVEAEDLGV YFCSQSTHIP YTFGGGTKLE IK |
| OGD201 VL43 (SEQ id no 101) | | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCQQSTHIP YTFGGGTKLE IK |
| OGD201 VL44 (SEQ id no 102) | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCMQSTHIP YTFGGGTKLE IK |
| OGD201 VL45 (SEQ id no 103) | | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQATHIP YTFGGGTKLE IK |
| OGD201 VL46 (SEQ id no 104) | − | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQGTHIP YTFGGGTKLE IK |
| OGD201 VL47 (SEQ id no 105) | | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSYHIP YTFGGGTKLE IK |
| OGD201 VL48 (SEQ id no 106) | − | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSLHIP YTFGGGTKLE IK |
| OGD201 VL49 (SEQ id no 107) | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTQIP YTFGGGTKLE IK |
| OGD201 VL50 (SEQ id no 108) | | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTNIP YTFGGGTKLE IK |
| OGD201 VL51 (SEQ id no 109) | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHTP YTFGGGTKLE IK |
| OGD201 VL52 (SEQ id no 110) | − | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHWP YTFGGGTKLE IK |
| OGD201 VL53 (SEQ id no 111) | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHIS YTFGGGTKLE IK |
| OGD201 Consensus 3 VL (SEQ id no 112) | | D/EV/IVMTQSPL/AS/T LP/SV/L/AS/TL/P/VGD/QEQ/P/RA/VS/T I/LS/TCRS/ASQSL/VL/V KN/SN/QG/A/SN/Y/ST/N/SF/YLH/N/S/A/Y/GW Y/FL/QQK/RPGQ/KS/A/VPK/Q/R L/R/VLIYK/G/LV/A/GSN/TRL/D/A S/TGV/IPD/A/SRFSGS GSGTY/DFTLK/TI S/NR/SV/LE/QA/PEDL/V/FG/AV/T YF/YCS/M/QQS/AT/YH/Q/NI/TP/S YTFGG/QGTKVE IK |

CDRs are represented in bold and mutated amino-acid mutated are highlight in grey.

1.5 Humanization 3$^{rd}$ Round:

On the basis of the optimization step done previously and of the corresponding consensus sequences, the inventors designed new humanized VH and VL sequences that were tested for their binding to OAcGD2.

After incubation and washes, antibody binding is detected by incubation with a goat anti-mouse IgG coupled with FITC (SOUTHERN BIOTECH) for 30 min on ice. Finally, cell fluorescence is analyzed by flow cytometer.

Surprisingly, the results show that, whereas VH72Bmax, VH49B, VH49Bmax, VL30BH, and VL28Bs01/A2 have been far modified as compared to their mouse counterpart,

| Name | Germline degree (%) | OAcGD2 binding | Amino-acid sequence |
|---|---|---|---|
| 8B6 VH (reference; SEQ id no 1) | 74 | + | EVKLVESGGG LVLPGDSLRL SCATSEFTFT DYYMTWVRQP PRKALEWLGF IRNRANGYTT EYNPSVKGRF TISRDNSQSI LYLQMNTLRT EDSATYYCAR VSNWAFDYWG QGTTLTVSS |
| OGD201 Consensus 3 VH (SEQ id no 76) | — | | EE/QVQLV/LESGGG LVQ/KPGG/RSLRL SCA/TT/ASE/GFTFT/S/G DY/HYMT/H/N/* SWV/IRQA PGKGLEWL/VG/SF/Y I/TRNR/K/SA/SNG/A/SY/GT/IT/I E/YYN/AP/A/DSVKGRF TISRDN/GS/AKS/NI/S/T L/T/AYLQMNSLR/K/QT/A EDTAV/T/LYYCA/TR VSNW/YA/YFDYWG QGTT/LL/VTVSS |
| OGD201 VH72max (SEQ id no 131) | 95 | + | EVQLVESGGG LVQPGGSLRL SCAASGFTFS DHYMTWVRQA PGKGLEWLGF IRNKANSYTT EYAASVKGRF TISRDNSKNS LYLQMNSLKT EDTAVYYCAR VSNWAFDYWG QGTLVTVSS |
| OGD201 VH49B SEQ id no 132) | 91 | + | EVQLVESGGG LVQPGRSLRL SCTASGFTFS DYYMTWVRQA PGKGLEWLGF IRNKANGYTT EYAASVKGRF TISRDNSKSI LYLQMNSLKT EDTAVYYCAR VSNWAFDYWG QGTLVTVSS |
| OGD201 VH49Bmax (SEQ id no 133) | 95 | + | EVQLVESGGG LVQPGRSLRL SCTASGFTFG DYYMSWVRQA PGKGLEWLGF IRNKANGGTT EYAASVKGRF TISRDNSKSI AYLQMNSLKT EDTAYYCER VSNWAFDYWG QGTTVTVSS |
| 8B6 VL SEQ id no 6) | 77 | + | DVVMTQTPLS LPVSLGDQAS ISCRSSQSLL KNNGNTFLHW YLQKSGQSPK LLIYKVSNRL SGVPDRFSGS GSGTYFTLKI SRVEAEDLGV YFCSQSTHIP YTFGGGTKLE IK |
| OGD201 Consensus 3 VL (SEQ id no 112) | — | | D/EV/IVMTQSPL/AS/T LP/SV/L/AS/TL/P/VGD/Q/EQ/P/RA/VS/T I/LS/TCRS/ASQSL/VL/V KN/SN/QG/A/SN/Y/ST/N/SF/YLH/N/S/A/Y/GW Y/FL/QQK/RPGQ/KS/A/VPK/Q/R L/R/VLIYK/G/LV/A/GSN/TRL/D/A S/TGV/IPD/A/SRFSGS GSGTY/DFTLK/TI S/NR/SV/LE/QA/PEDL/V/FG/AV/T YF/YCS/M/QQS/AT/YH/Q/NI/TP/S YTFGG/QGTKVE IK |
| OGD201 VL30BH SEQ id no 134) | 90 | + | DVVMTQSPLS LPVTLGQPAS ISCRSSQSLV KNQGNTFLHW KQQRPGQSPR LLIYKVSNRL SGVPDRFSGS GSGTDFTLKI SRVEAEDVGV YYCSQSTHIP YTFGGGTKVE IK |
| OGD201 VL28Bs01/A2 SEQ id no 135) | 86 | + | DVVMTQSPLS LPVTPGKPAS ISCRSSQSLL KSNANTFLHW YLQKPGQSPQ LLIYKVSNRL SGVPDRFSGS GSGTDFTLKI SRVEAEDVGV YYCMQSTHIP YTFGQGTKVE IK |

CDRs are represented in bold and mutated amino-acid mutated are highlighted in grey.

Then, the binding of the obtained humanized antibodies is tested by their incubation at different concentrations—i.e. 0.01 to 10 μg/ml—on IMR5 cells—i.e. expressing OAcGD2 at their surface—in PBS, 1% BSA for 45 minutes on ice.

they have got a binding affinity comparable to this mouse counterpart, VH49Bmax and VL28Bs01/A2 having the better one.

2) scFv Constructs

The selected humanized VH and VL sequences are fused together in VH-Linker-VL or VL-Linker-VH orientation using the linkers disclosed in table 5. For simplifying the step of purification of these polypeptides various tags could be added in C-terminal extremity, preferably a His Tag (HHHHHH; SEQ ID NO:125).

TABLE 5

Linker

| "Name" | Linker sequence |
|---|---|
| (G4S)3 (SEQ ID NO: 116) | GGGGSGGGGSGGGGS |
| CD19 linker (SEQ ID NO: 117) | GSTSGSGKPGSGEGSTKG |
| 18mer (SEQ ID NO: 118) | GGSSRSSSSGGGGSGGGG |
| (G4S)4 (SEQ ID NO: 119) | GGGGSGGGGSGGGGSGGGGS |
| (SEQ ID NO: 120) | KESGSVSSEQLAQFRSLD |
| (SEQ ID NO: 121) | EGKSSGSGSESKST |
| (SEQ ID NO: 122) | GSAGSAAGSGEF |
| (SEQ ID NO: 123) | GGGGGGGG |
| (SEQ ID NO: 124) | GGGGGG |

Then, the designed scFv fragments are produced in *E. coli* system or mammalian including CHO, Sp2/O, HEK 293 and further purified by affinity chromatography depending of the used tags (e.g. nickel chelated with nickel ions for His tag).

3) $K_d$ Determination

The affinity of humanized antibodies and fragments thereof (scFv) is assessed using a BIACORE T200 BIOSENSOR (GE HEALTHCARE). For these experiments, gangliosides (OAcGD2, GD2, GM2) are directly immobilized onto the CMS biosensor chip via hydrophobic interaction. For this, ganglioside diluted mixtures (50 µg/ml) are injected (75 µl) at a flow rate of 5 µl/min during 15 min.

Then, increasing concentration (6.25 to 200 nM) of purified antibody or fragment thereof (scFv) diluted in HBS-E buffer containing 250 mM NaCl are prepared. The samples (60 µl) to be tested are injected over the sensor surface at a flow rate of 30 µl/min over 2 min.

Finally, the binding data are analyzed by a bivalent analysis model and default parameter settings for the rate constants using the BIACORE T-200 evaluation software.

| Name | SEQ ID NO: | $K_d$(M) |
|---|---|---|
| 8B6 | — | 3.26E-07 |
| OGD201 VL1 | 8 | 2.87E-07 |
| OGD201 VL2 | 9 | 3.20E-07 |
| OGD201 VL3 | 10 | 3.41E-07 |
| OGD201 VL4 | 11 | 4.82E-07 |
| OGD201 VL5 | 30 | 3.19E-07 |
| OGD201 VL6 | 31 | ND |
| OGD201 VL7 | 32 | 3.31E-07 |
| OGD201 VL8 | 33 | 3.02E-07 |
| OGD201 VL9 | 34 | 5.58E-07 |
| OGD201 VL10 | 35 | 2.85E-07 |
| OGD201 VL11 | 36 | 4.82E-07 |
| OGD201 VL14 | 39 | 2.63E-07 |
| OGD201 VH1 | 3 | 2.67E-07 |
| OGD201 VH2 | 4 | 1.81E-07 |
| OGD201 VH3 | 5 | 2.16E-07 |
| OGD201 VH5 | 13 | 2.08E-07 |
| OGD201 VH6 | 14 | 4.64E-07 |
| OGD201 VH8 | 17 | ND |
| OGD201 VH9 | 18 | 1.80E-07 |
| OGD201 VH10 | 19 | 2.87E-07 |
| OGD201 VH11 | 20 | 2.72E-07 |
| OGD201 VH12 | 21 | ND |
| OGD201 VH14 | 23 | 2.58E-07 |
| OGD201 VH17 | 26 | ND |

4) Cytotoxic Activity Determination

Direct cytotoxicity of purified humanized antibodies or fragments thereof is analyzed by propidium iodide incorporation (PI).

In IP assays, $1 \times 10^5$ IMR5 cells are incubated 24h at 37° C. in a 48-well plate. 40 µg/ml of antibodies or fragments thereof are added and incubated 16h at 37° C. After incubation, PI at 10 µg/ml in PBS is added and the fluorescence is immediately analyzed by flow cytometry. Percentage of death cells were represented as mean±SD in triplicate.

ADCC activity was determined as follow. Tumor cells were labeled with membrane dye PKH-26 (Sigma Aldrich) according to the manufacturer's instructions. Labeled cells ($10^4$ cells in 100 µL) were incubated with 50 µL of antibodies in 96-well microtiter plates. The human cells line NK-92-RFcgIII+, or total PBMC, were used as effector cells. Effector cells (50 µL) at the indicated effector-to-target ratio were added to the tumor cells and incubated for 24 hours at 37° C. Cell death within the PKH-26+ target cell population was then assessed by the addition of TOPRO-3 iodide (TP3) (Life Technologies). The double-positive TP3+, PKH26+ dead target cell population was detected by flow cytometry. The percentage of specific lysis was calculated as: 100×(non viable double-positive target cells)/(non viable double-positive target cells+viable PKH26+ target cells).

5) Immunogenicity Determination

To study the immunogenicity potential of the antibodies, we used the PROPRESENT® Antigen Presentation Assays (PROIMMUNE) or EPISCREEN (ANTITOPE) or EPIBASE T CELL assays (LONZA) or IMMUNO'LINE (PLATINE) as well.

Briefly, a panel of HLA-typed, healthy donor peripheral blood mononuclear cell (PBMC) samples are prepared from tissue bank (selected to reflect HLA distribution of choice). Then, monocytes from donor PBMC are cultured in defined media and differentiated to produce dendritic cells (DC).

For analysis for T cell activation, we used the DC loaded with the test antigen (i.e. antibodies to be tested) in presence to CD4+ T cells. Finally, T cell activation is measured by T cell proliferation assays (i.e. CFSE, $H^3$) and cytokine secretion (i.e. IL-2, IL-6, IL-8, INFγ). Significant T cell responses are determined by parametric and non-parametric statistical analysis. Results are benchmarked to internal control.

To identifying sequence of interest, we used harvested DC, and purified corresponding HLA molecules. Associated peptides are eluted. The peptide samples are analyzed by sequencing mass spectrometry and the obtained data are then compared against a protein database library consisting of the sequence of interest and the international protein index (IPI) of the organism of choice. The peptides are ranked by significance according to a probability based algorithm and the data are verified by searching against a scrambled decoy database to reduce false positives.

Finally, the obtained data enable to determine the potential immunogenicity in human of the tested antibodies.

6) Cytokine Release Assay

Total PBMC are incubated with humanized antibodies and fragments thereof (scFv) or with the control mouse antibody (8B6) and the cytokines secretion (IFN gamma, TNF alpha, IL-6, IL-2, IL-10, IL-12, IL-13, IL-17, IL-1 beta, . . . ) is analyzed by the Bio-Plex Precision Pro™ human cytokine immunoassay (BIORAD) according to the manufacturer's instructions. For more details, see FINCO et al. (Cytokine, vol. 66, p: 143-145, 2014).

Finally, the cytokine expression profiles enable to determine the potential immunogenicity in human of the tested antibodies.

Surprisingly, the immunogenicity results show that, whereas VH72Bmax, VH49B, VH49Bmax, VL30BH, and VL28Bs01/A2 have a binding affinity for OAcGD2 and GD2 gangliosides comparable to their mouse counterpart, they have a weaken immunogenicity, VH72max and VH49Bmax having the weakest one.

Now and still surprisingly, the immunogenicity results also show that, whereas VH1, VH2, VH3, VH72BCDR, VH72BH, VH49BCDR, VH49BH, VL1, VL2, VL3, VL4, and VL28BH have a binding affinity as good as their mouse counterpart, they have also a smallest immunogenicity.

The invention claimed is:

1. An antibody, functional fragment, or derivative thereof, which binds specifically to the O-acetylated GD2 (OAcGD2) ganglioside, said antibody, functional fragment or derivative thereof comprising:
   a) a humanized light chain variable region (VL) polypeptide having the amino acid sequence SEQ ID NO: 112; and
   b) a humanized heavy chain variable region (VH) having the amino acid sequence SEQ ID NO: 76.

2. The antibody of claim 1, wherein said antibody, functional fragment or derivative thereof comprises:
   the light chain variable region (VL) having the amino acid sequence selected in the group comprising VL30BH (SEQ ID NO: 134) and VL28Bs01/A2 (SEQ ID NO: 135), and/or
   the heavy chain variable region (VH) having the amino acid sequence selected in the group comprising VH72Bmax (SEQ ID NO: 131), VH49B (SEQ ID NO: 132), and VH49Bmax (SEQ ID NO: 133).

3. The antibody of claim 1, wherein said antibody, functional fragment or derivative thereof comprises:
   the light chain variable region (VL) having the amino acid sequence selected in the group comprising VL1 (SEQ ID NO: 8), VL2 (SEQ ID NO: 9), VL3 (SEQ ID NO: 10), VL4 (SEQ ID NO: 11), VL28BH (SEQ ID NO: 140), VL30BH (SEQ ID NO: 134) and VL28Bs01/A2 (SEQ ID NO: 135) and/or
   the heavy chain variable region (VH) having the amino acid sequence selected in the group comprising VH1 (SEQ ID NO: 3), VH2 (SEQ ID NO: 4), and VH3 (SEQ ID NO: 5), VH72BCDR (SEQ ID NO: 136), VH72BH (SEQ ID NO: 137), VH49BCDR (SEQ ID NO: 138), VH49BH (SEQ ID NO: 139), VH72Bmax (SEQ ID NO: 131), VH49B (SEQ ID NO: 132); and VH49Bmax (SEQ ID NO: 133).

4. The antibody of claim 1, wherein said antibody, functional fragment or derivative thereof, which binds specifically to the OAcGD2 ganglioside presents a $K_d$ of less than $5 \times 10^{-6}$ M for said ganglioside at 25° C.

5. The antibody of claim 1, wherein said antibody, functional fragment or derivative thereof, which binds specifically to the OAcGD2 ganglioside presents a binding affinity ($K_d$) of more than $5 \times 10^{-5}$ M at 25° C. for GD2 ganglioside.

6. The antibody of claim 1, wherein the antibody functional fragments or derivatives thereof comprises at least both of said heavy and light chains variable regions.

7. The antibody of claim 1, wherein the antibody functional fragments or derivatives thereof are the membrane anchored single-chain variable part of a chimeric antigen receptor (CAR).

8. The antibody of claim 7, wherein said CAR comprises an ectodomain, a transmembrane domain and an endodomain.

9. The antibody of claim 1, wherein said antibody is an immunoconjugate.

10. The antibody of claim 1, wherein said functional fragments is selected in the group comprising ScFv fragment, $F_{ab}$ fragment, $F_{ab}'$ fragment, $F(_{ab}')_2$ fragment, $F_{acb}$ fragment, $F_v$ and $F_d$ fragments.

11. A pharmaceutical composition comprising at least one antibody, functional fragment or derivative thereof according to claim 1, and a pharmaceutically acceptable carrier.

12. The pharmaceutical composition as defined in claim 11 for use in a method of preventing and/or treating cancer expressing the OAcGD2 ganglioside in a subject.

13. The pharmaceutical composition of claim 12, wherein said subject is a mammal.

14. The pharmaceutical composition of claim 12 wherein said cancer expressing the OAcGD2 ganglioside is selected in the group comprising neuroblastoma, glioma, retinoblastoma, Ewing's family of tumors, sarcoma, small cell lung cancer, breast cancer, melanoma, metastatic renal carcinoma, head and neck cancer and hematological cancer.

15. A method for diagnosing a cancer expressing OAcGD2 ganglioside in a subject comprising the step of contacting a biological sample of said subject with at least one antibody, functional fragment or derivative thereof as defined in claim 1, for determining an OAcGD2 ganglioside expression level in said biological sample, wherein a detectable OAcGD2 ganglioside expression level is indicative of such a cancer.

16. A kit for diagnosing a cancer expressing the OAcGD2 ganglioside in a subject, which comprises at least one antibody, functional fragment or derivative thereof as defined in claim 1.

17. The antibody of claim 1, wherein said antibody, functional fragment or derivative thereof, which binds specifically to the OAcGD2 ganglioside presents a $K_d$ of equal to or less than $5 \times 10^{-7}$ M, for said ganglioside at 25° C.

18. The antibody of claim 1, wherein said antibody, functional fragment or derivative thereof, which binds specifically to the OAcGD2 ganglioside presents a $K_d$ of equal to or less than $5 \times 10^{-8}$ M, for said ganglioside at 25° C.

19. The antibody of claim 1, wherein said antibody, functional fragment or derivative thereof, which binds specifically to the OAcGD2 ganglioside presents a binding affinity ($K_d$) of more than $10^{-5}$ M at 25° C. for GD2 ganglioside.

20. The pharmaceutical composition of claim 13, wherein the subject is a human.

21. A method for treating a cancer expressing OAcGD2 in a subject in need thereof comprising administering to said subject an effective amount of at least one antibody, functional fragment or derivative thereof according to claim 1.

* * * * *

SEQUENCE LISTING

```
<160> NUMBER OF SEQ ID NOS: 140

<210> SEQ ID NO 1
<211> LENGTH: 119
<212> TYPE: PRT
<213> ORGANISM: Mus musculus

<400> SEQUENCE: 1

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: OGD201 Consensus sequence for first humanized
      VH sequence
<220> FEATURE:
<221> NAME/KEY: MISC_FEATURE
<222> LOCATION: (1)..(1)
<223> OTHER INFORMATION: X = E or Q
<220> FEATURE:
<221> NAME/KEY: MISC_FEATURE
<222> LOCATION: (13)..(13)
<223> OTHER INFORMATION: X = Q or K
<220> FEATURE:
<221> NAME/KEY: MISC_FEATURE
<222> LOCATION: (16)..(16)
<223> OTHER INFORMATION: X = G or R
<220> FEATURE:
<221> NAME/KEY: MISC_FEATURE
<222> LOCATION: (23)..(23)
<223> OTHER INFORMATION: X = A or T
<220> FEATURE:
<221> NAME/KEY: MISC_FEATURE
<222> LOCATION: (77)..(77)
<223> OTHER INFORMATION: X = S or A
<220> FEATURE:
```

```
<221> NAME/KEY: MISC_FEATURE
<222> LOCATION: (79)..(79)
<223> OTHER INFORMATION: X = S or N
<220> FEATURE:
<221> NAME/KEY: MISC_FEATURE
<222> LOCATION: (80)..(80)
<223> OTHER INFORMATION: X = I or S
<220> FEATURE:
<221> NAME/KEY: MISC_FEATURE
<222> LOCATION: (89)..(89)
<223> OTHER INFORMATION: X = R or K
<220> FEATURE:
<221> NAME/KEY: MISC_FEATURE
<222> LOCATION: (90)..(90)
<223> OTHER INFORMATION: X = T or A

<400> SEQUENCE: 2

Xaa Val Gln Leu Val Glu Ser Gly Gly Gly Leu Val Xaa Pro Gly Xaa
1               5                   10                  15

Ser Leu Arg Leu Ser Cys Xaa Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Xaa Lys Xaa Xaa
65                  70                  75                  80

Leu Tyr Leu Gln Met Asn Ser Leu Xaa Xaa Glu Asp Thr Ala Val Tyr
                85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115

<210> SEQ ID NO 3
<211> LENGTH: 119
<212> TYPE: PRT
<213> ORGANISM: Artificial Sequence
<220> FEATURE:
<223> OTHER INFORMATION: OGD201 VH1

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
                100                 105                 110

Thr Leu Val Thr Val Ser Ser
            115

<210> SEQ ID NO 4
<211> LENGTH: 119
```

```
<212> TYPE: PRT
<213> ORGANISM: Artificial Sequence
<220> FEATURE:
<223> OTHER INFORMATION: OGD201 VH2

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Thr Thr Ser Glu Phe Thr Phe Thr Asp Tyr
                20                  25                  30

Tyr Met Thr Trp Val Arg Gln Ala Pro Gly Lys Gly Leu Glu Trp Leu
            35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: 201 VH3-11*01A

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Thr Ser Glu Phe Thr Phe Thr Asp Tyr
                20                  25                  30

Tyr Met Thr Trp Val Arg Gln Ala Pro Gly Lys Gly Leu Glu Trp Leu
            35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 6
<211> LENGTH: 112
<212> TYPE: PRT
<213> ORGANISM: Mus musculus

<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                20                  25                  30
```

```
Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65              70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: OGD201 Consensus sequence for first humanized
      VL sequence
<220> FEATURE:
<221> NAME/KEY: MISC_FEATURE
<222> LOCATION: (1)..(1)
<223> OTHER INFORMATION: X = D or E
<220> FEATURE:
<221> NAME/KEY: MISC_FEATURE
<222> LOCATION: (3)..(3)
<223> OTHER INFORMATION: X = V or Q
<220> FEATURE:
<221> NAME/KEY: MISC_FEATURE
<222> LOCATION: (9)..(9)
<223> OTHER INFORMATION: X = L or A
<220> FEATURE:
<221> NAME/KEY: MISC_FEATURE
<222> LOCATION: (10)..(10)
<223> OTHER INFORMATION: X = S or T
<220> FEATURE:
<221> NAME/KEY: MISC_FEATURE
<222> LOCATION: (12)..(12)
<223> OTHER INFORMATION: X = P or S
<220> FEATURE:
<221> NAME/KEY: MISC_FEATURE
<222> LOCATION: (13)..(13)
<223> OTHER INFORMATION: X = V or L or A
<220> FEATURE:
<221> NAME/KEY: MISC_FEATURE
<222> LOCATION: (14)..(14)
<223> OTHER INFORMATION: X = S or T
<220> FEATURE:
<221> NAME/KEY: MISC_FEATURE
<222> LOCATION: (15)..(15)
<223> OTHER INFORMATION: X = L or P or V
<220> FEATURE:
<221> NAME/KEY: MISC_FEATURE
<222> LOCATION: (17)..(17)
<223> OTHER INFORMATION: X = D or Q or E
<220> FEATURE:
<221> NAME/KEY: MISC_FEATURE
<222> LOCATION: (18)..(18)
<223> OTHER INFORMATION: X =Q or P or R
<220> FEATURE:
<221> NAME/KEY: MISC_FEATURE
<222> LOCATION: (19)..(19)
<223> OTHER INFORMATION: X = A or V
<220> FEATURE:
<221> NAME/KEY: MISC_FEATURE
<222> LOCATION: (20)..(20)
<223> OTHER INFORMATION: X = S or T
<220> FEATURE:
<221> NAME/KEY: MISC_FEATURE
<222> LOCATION: (21)..(21)
<223> OTHER INFORMATION: X = I or L
<220> FEATURE:
<221> NAME/KEY: MISC_FEATURE
<222> LOCATION: (22)..(22)
<223> OTHER INFORMATION: X = S or T -continued

```
<220> FEATURE:
<221> NAME/KEY: MISC_FEATURE
<222> LOCATION: (42)..(42)
<223> OTHER INFORMATION: X = L or Q
<220> FEATURE:
<221> NAME/KEY: MISC_FEATURE
<222> LOCATION: (44)..(44)
<223> OTHER INFORMATION: X = K or R
<220> FEATURE:
<221> NAME/KEY: MISC_FEATURE
<222> LOCATION: (47)..(47)
<223> OTHER INFORMATION: X = Q or K
<220> FEATURE:
<221> NAME/KEY: MISC_FEATURE
<222> LOCATION: (48)..(48)
<223> OTHER INFORMATION: X = S or A
<220> FEATURE:
<221> NAME/KEY: MISC_FEATURE
<222> LOCATION: (50)..(50)
<223> OTHER INFORMATION: X = K or Q or R
<220> FEATURE:
<221> NAME/KEY: MISC_FEATURE
<222> LOCATION: (61)..(61)
<223> OTHER INFORMATION: X = S or T
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (65)..(65)
<223> OTHER INFORMATION: X =D or A or S
<220> FEATURE:
<221> NAME/KEY: MISC_FEATURE
<222> LOCATION: (75)..(75)
<223> OTHER INFORMATION: X =Y or D
<220> FEATURE:
<221> NAME/KEY: MISC_FEATURE
<222> LOCATION: (79)..(79)
<223> OTHER INFORMATION: X =K or T
<220> FEATURE:
<221> NAME/KEY: MISC_FEATURE
<222> LOCATION: (82)..(82)
<223> OTHER INFORMATION: X = R or S
<220> FEATURE:
<221> NAME/KEY: MISC_FEATURE
<222> LOCATION: (83)..(83)
<223> OTHER INFORMATION: X = V or L
<220> FEATURE:
<221> NAME/KEY: MISC_FEATURE
<222> LOCATION: (84)..(84)
<223> OTHER INFORMATION: X = E or Q
<220> FEATURE:
<221> NAME/KEY: MISC_FEATURE
<222> LOCATION: (85)..(85)
<223> OTHER INFORMATION: X = A or P
<220> FEATURE:
<221> NAME/KEY: MISC_FEATURE
<222> LOCATION: (88)..(88)
<223> OTHER INFORMATION: X = L or V or F
<220> FEATURE:
<221> NAME/KEY: MISC_FEATURE
<222> LOCATION: (89)..(89)
<223> OTHER INFORMATION: X = G or A
<220> FEATURE:
<221> NAME/KEY: MISC_FEATURE
<222> LOCATION: (90)..(90)
<223> OTHER INFORMATION: X = V or T
<220> FEATURE:
<221> NAME/KEY: MISC_FEATURE
<222> LOCATION: (92)..(92)
<223> OTHER INFORMATION: X = Y or F
<220> FEATURE:
<221> NAME/KEY: MISC_FEATURE
<222> LOCATION: (105)..(105)
<223> OTHER INFORMATION: X = G or Q

<400> SEQUENCE: 7
```

Xaa Val Xaa Met Thr Gln Ser Pro Xaa Xaa Leu Xaa Xaa Xaa Xaa Gly
1               5                   10                  15

Xaa Xaa Xaa Xaa Xaa Xaa Cys Arg Ser Ser Gln Ser Leu Leu Lys Asn
                20                  25                  30

Asn Gly Asn Thr Phe Leu His Trp Tyr Xaa Gln Xaa Pro Gly Xaa Xaa
            35                  40                  45

Pro Xaa Leu Leu Ile Tyr Lys Val Ser Asn Arg Leu Xaa Gly Xaa Pro
    50                  55                  60

Xaa Arg Phe Ser Gly Ser Gly Ser Gly Thr Xaa Phe Thr Leu Xaa Ile
65              70                  75                  80

Ser Xaa Xaa Xaa Xaa Glu Asp Xaa Xaa Xaa Tyr Xaa Cys Ser Gln Ser
        85                  90                  95

Thr His Ile Pro Tyr Thr Phe Gly Xaa Gly Thr Lys Val Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: OGD201 VL1

<400> SEQUENCE: 8

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Lys Asn
                20                  25                  30

Asn Gly Asn Thr Phe Leu His Trp Tyr Gln Gln Arg Pro Gly Gln Ser
            35                  40                  45

Pro Arg Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Phe Cys Ser Gln Ser
        85                  90                  95

Thr His Ile Pro Tyr Thr Phe Gly Gly Gly Thr Lys Val Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: OGD201 VL2

<400> SEQUENCE: 9

Glu Val Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Lys Asn
                20                  25                  30

Asn Gly Asn Thr Phe Leu His Trp Tyr Gln Gln Lys Pro Gly Gln Ala
            35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65              70                  75                  80

Ser Ser Leu Gln Pro Glu Asp Phe Ala Val Tyr Phe Cys Ser Gln Ser
        85                  90                  95

```
Thr His Ile Pro Tyr Thr Phe Gly Gly Gly Thr Lys Val Glu Ile Lys
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: OGD201 VL3

<400> SEQUENCE: 10

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Lys Asn
            20                  25                  30

Asn Gly Asn Thr Phe Leu His Trp Tyr Leu Gln Lys Pro Gly Gln Ser
        35                  40                  45

Pro Gln Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Ile Pro Tyr Thr Phe Gly Gln Gly Thr Lys Val Glu Ile Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: OGD201 VL4

<400> SEQUENCE: 11

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Lys Asn
            20                  25                  30

Asn Gly Asn Thr Phe Leu His Trp Tyr Gln Gln Lys Pro Gly Lys Ala
        35                  40                  45

Pro Lys Leu Leu Ile Tyr Lys Val Ser Asn Arg Leu Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Val Ala Thr Tyr Tyr Cys Ser Gln Ser
                85                  90                  95

Thr His Ile Pro Tyr Thr Phe Gly Gln Gly Thr Lys Val Glu Ile Lys
            100                 105                 110

<210> SEQ ID NO 12
<211> LENGTH: 119
<212> TYPE: PRT
<213> ORGANISM: Artificial Sequence
<220> FEATURE:
<223> OTHER INFORMATION: OGD201 Consensus sequence for second humanized
      VH sequence
<220> FEATURE:
<221> NAME/KEY: MISC_FEATURE
<222> LOCATION: (1)..(1)
<223> OTHER INFORMATION: X=E or Q
<220> FEATURE:
```

```
<221> NAME/KEY: MISC_FEATURE
<222> LOCATION: (5)..(5)
<223> OTHER INFORMATION: X=V or L
<220> FEATURE:
<221> NAME/KEY: MISC_FEATURE
<222> LOCATION: (13)..(13)
<223> OTHER INFORMATION: X=Q or K
<220> FEATURE:
<221> NAME/KEY: MISC_FEATURE
<222> LOCATION: (16)..(16)
<223> OTHER INFORMATION: X= G or R
<220> FEATURE:
<221> NAME/KEY: MISC_FEATURE
<222> LOCATION: (23)..(23)
<223> OTHER INFORMATION: X= A or T
<220> FEATURE:
<221> NAME/KEY: MISC_FEATURE
<222> LOCATION: (24)..(24)
<223> OTHER INFORMATION: X= T or A
<220> FEATURE:
<221> NAME/KEY: MISC_FEATURE
<222> LOCATION: (48)..(48)
<223> OTHER INFORMATION: X= L or V
<220> FEATURE:
<221> NAME/KEY: MISC_FEATURE
<222> LOCATION: (49)..(49)
<223> OTHER INFORMATION: X= G or S
<220> FEATURE:
<221> NAME/KEY: MISC_FEATURE
<222> LOCATION: (57)..(57)
<223> OTHER INFORMATION: X= G or A
<220> FEATURE:
<221> NAME/KEY: MISC_FEATURE
<222> LOCATION: (63)..(63)
<223> OTHER INFORMATION: X= N or A
<220> FEATURE:
<221> NAME/KEY: MISC_FEATURE
<222> LOCATION: (64)..(64)
<223> OTHER INFORMATION: X= P or A
<220> FEATURE:
<221> NAME/KEY: MISC_FEATURE
<222> LOCATION: (77)..(77)
<223> OTHER INFORMATION: X= S or A
<220> FEATURE:
<221> NAME/KEY: MISC_FEATURE
<222> LOCATION: (79)..(79)
<223> OTHER INFORMATION: X= S or N
<220> FEATURE:
<221> NAME/KEY: MISC_FEATURE
<222> LOCATION: (80)..(80)
<223> OTHER INFORMATION: X= I or S or T
<220> FEATURE:
<221> NAME/KEY: MISC_FEATURE
<222> LOCATION: (81)..(81)
<223> OTHER INFORMATION: X= L or T
<220> FEATURE:
<221> NAME/KEY: MISC_FEATURE
<222> LOCATION: (89)..(89)
<223> OTHER INFORMATION: X= R or K or Q
<220> FEATURE:
<221> NAME/KEY: MISC_FEATURE
<222> LOCATION: (90)..(90)
<223> OTHER INFORMATION: X= T or A
<220> FEATURE:
<221> NAME/KEY: MISC_FEATURE
<222> LOCATION: (95)..(95)
<223> OTHER INFORMATION: X= V or I
<220> FEATURE:
<221> NAME/KEY: MISC_FEATURE
<222> LOCATION: (114)..(114)
<223> OTHER INFORMATION: X= T or L
<220> FEATURE:
<221> NAME/KEY: MISC_FEATURE
<222> LOCATION: (115)..(115)
<223> OTHER INFORMATION: X= L or V

<400> SEQUENCE: 12

Xaa Val Gln Leu Xaa Glu Ser Gly Gly Gly Leu Val Xaa Pro Gly Xaa
```

```
                1               5                   10                  15
            Ser Leu Arg Leu Ser Cys Xaa Xaa Ser Glu Phe Thr Phe Thr Asp Tyr
                            20                  25                  30

Tyr Met Thr Trp Val Arg Gln Ala Pro Gly Lys Gly Leu Glu Trp Xaa
                        35                  40                  45

Xaa Phe Ile Arg Asn Arg Ala Asn Xaa Tyr Thr Thr Glu Tyr Xaa Xaa
                    50                  55                  60

Ser Val Lys Gly Arg Phe Thr Ile Ser Arg Asp Asn Xaa Lys Xaa Xaa
            65                  70                  75                  80

Xaa Tyr Leu Gln Met Asn Ser Leu Xaa Xaa Glu Asp Thr Ala Xaa Tyr
                            85                  90                  95

Tyr Cys Ala Arg Val Ser Asn Trp Ala Phe Asp Tyr Trp Gly Gln Gly
                            100                 105                 110

Thr Xaa Xaa Thr Val Ser Ser
                            115

<210> SEQ ID NO 13
<211> LENGTH: 119
<212> TYPE: PRT
<213> ORGANISM: Artificial Sequence
<220> FEATURE:
<223> OTHER INFORMATION: OGD201 VH VH4

<400> SEQUENCE: 13

Glu Val Lys Leu Leu Glu Ser Gly Gly Gly Leu Val Leu Pro Gly Asp
            1               5                   10                  15

Ser Leu Arg Leu Ser Cys Ala Thr Ser Glu Phe Thr Phe Thr Asp Tyr
                            20                  25                  30

Tyr Met Thr Trp Val Arg Gln Pro Pro Arg Lys Ala Leu Glu Trp Leu
                        35                  40                  45

Gly Phe Ile Arg Asn Arg Ala Asn Gly Tyr Thr Thr Glu Tyr Asn Pro
                    50                  55                  60

Ser Val Lys Gly Arg Phe Thr Ile Ser Arg Asp Asn Ser Gln Ser Ile
            65                  70                  75                  80

Leu Tyr Leu Gln Met Asn Thr Leu Arg Thr Glu Asp Ser Ala Thr Tyr
                            85                  90                  95

Tyr Cys Ala Arg Val Ser Asn Trp Ala Phe Asp Tyr Trp Gly Gln Gly
                            100                 105                 110

Thr Thr Leu Thr Val Ser Ser
                            115

<210> SEQ ID NO 14
<211> LENGTH: 119
<212> TYPE: PRT
<213> ORGANISM: Artificial Sequence
<220> FEATURE:
<223> OTHER INFORMATION: OGD201 VH5

<400> SEQUENCE: 14

Glu Val Lys Leu Val Glu Ser Gly Gly Gly Leu Val Leu Pro Gly Asp
            1               5                   10                  15

Ser Leu Arg Leu Ser Cys Ala Ala Ser Glu Phe Thr Phe Thr Asp Tyr
                            20                  25                  30

Tyr Met Thr Trp Val Arg Gln Pro Pro Arg Lys Ala Leu Glu Trp Leu
                        35                  40                  45

Gly Phe Ile Arg Asn Arg Ala Asn Gly Tyr Thr Thr Glu Tyr Asn Pro
                    50                  55                  60
```

```
Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 15
<211> LENGTH: 119
<212> TYPE: PRT
<213> ORGANISM: Artificial Sequence
<220> FEATURE:
<223> OTHER INFORMATION: OGD201 VH6

<400> SEQUENCE: 15

Glu Val Lys Leu Val Glu Ser Gly Gly Gly Leu Val Leu Pro Gly Asp
  1               5                  10                  15

Ser Leu Arg Leu Ser Cys Ala Thr Ser Glu Phe Thr Phe Thr Asp Tyr
                 20                  25                  30

Tyr Met Thr Trp Val Arg Gln Pro Pro Arg Lys Ala Leu Glu Trp Val
             35                  40                  45

Gly Phe Ile Arg Asn Arg Ala Asn Gly Tyr Thr Thr Glu Tyr Asn Pro
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 16
<211> LENGTH: 119
<212> TYPE: PRT
<213> ORGANISM: Artificial Sequence
<220> FEATURE:
<223> OTHER INFORMATION: OGD201 VH7

<400> SEQUENCE: 16

Glu Val Lys Leu Val Glu Ser Gly Gly Gly Leu Val Leu Pro Gly Asp
  1               5                  10                  15

Ser Leu Arg Leu Ser Cys Ala Thr Ser Glu Phe Thr Phe Thr Asp Tyr
                 20                  25                  30

Tyr Met Thr Trp Val Arg Gln Pro Pro Arg Lys Ala Leu Glu Trp Leu
             35                  40                  45

Ser Phe Ile Arg Asn Arg Ala Asn Gly Tyr Thr Thr Glu Tyr Asn Pro
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115
```

<210> SEQ ID NO 17
<211> LENGTH: 119
<212> TYPE: PRT
<213> ORGANISM: Artificial Sequence
<220> FEATURE:
<223> OTHER INFORMATION: OGD201 VH8

<400> SEQUENCE: 17

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Gln Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115
```

<210> SEQ ID NO 18
<211> LENGTH: 119
<212> TYPE: PRT
<213> ORGANISM: Artificial Sequence
<220> FEATURE:
<223> OTHER INFORMATION: OGD201 VH9

<400> SEQUENCE: 18

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Ala Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115
```

<210> SEQ ID NO 19
<211> LENGTH: 119
<212> TYPE: PRT
<213> ORGANISM: Artificial Sequence
<220> FEATURE:
<223> OTHER INFORMATION: OGD201 VH10

<400> SEQUENCE: 19

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Ala Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115
```

<210> SEQ ID NO 20
<211> LENGTH: 119
<212> TYPE: PRT
<213> ORGANISM: Artificial Sequence
<220> FEATURE:
<223> OTHER INFORMATION: OGD201 VH11

<400> SEQUENCE: 20

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115
```

<210> SEQ ID NO 21
<211> LENGTH: 119
<212> TYPE: PRT
<213> ORGANISM: Artificial Sequence
<220> FEATURE:
<223> OTHER INFORMATION: OGD201 VH12

<400> SEQUENCE: 21

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60
```

```
Ser Val Lys Gly Arg Phe Thr Ile Ser Arg Asp Asp Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 22
<211> LENGTH: 119
<212> TYPE: PRT
<213> ORGANISM: Artificial Sequence
<220> FEATURE:
<223> OTHER INFORMATION: OGD201 VH13

<400> SEQUENCE: 22

Glu Val Lys Leu Val Glu Ser Gly Gly Gly Leu Val Leu Pro Gly Asp
 1               5                   10                  15

Ser Leu Arg Leu Ser Cys Ala Thr Ser Glu Phe Thr Phe Thr Asp Tyr
                 20                  25                  30

Tyr Met Thr Trp Val Arg Gln Pro Pro Arg Lys Ala Leu Glu Trp Leu
             35                  40                  45

Gly Phe Ile Arg Asn Arg Ala Asn Gly Tyr Thr Thr Glu Tyr Asn Pro
     50                  55                  60

Ser Val Lys Gly Arg Phe Thr Ile Ser Arg Asp Asn Ser Gln Ser Thr
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 23
<211> LENGTH: 119
<212> TYPE: PRT
<213> ORGANISM: Artificial Sequence
<220> FEATURE:
<223> OTHER INFORMATION: OGD201 VH14

<400> SEQUENCE: 23

Glu Val Lys Leu Val Glu Ser Gly Gly Gly Leu Val Leu Pro Gly Asp
 1               5                   10                  15

Ser Leu Arg Leu Ser Cys Ala Thr Ser Glu Phe Thr Phe Thr Asp Tyr
                 20                  25                  30

Tyr Met Thr Trp Val Arg Gln Pro Pro Arg Lys Ala Leu Glu Trp Leu
             35                  40                  45

Gly Phe Ile Arg Asn Arg Ala Asn Gly Tyr Thr Thr Glu Tyr Asn Pro
     50                  55                  60

Ser Val Lys Gly Arg Phe Thr Ile Ser Arg Asp Asn Ser Gln Ser Ile
 65                  70                  75                  80

Thr Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
```

-continued

```
        115

<210> SEQ ID NO 24
<211> LENGTH: 119
<212> TYPE: PRT
<213> ORGANISM: Artificial Sequence
<220> FEATURE:
<223> OTHER INFORMATION: OGD201 VH15

<400> SEQUENCE: 24

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Gln Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 25
<211> LENGTH: 119
<212> TYPE: PRT
<213> ORGANISM: Artificial Sequence
<220> FEATURE:
<223> OTHER INFORMATION: OGD201 VH16

<400> SEQUENCE: 25

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Ile Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: OGD201 VH17

<400> SEQUENCE: 26
```

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Phe Ala Phe Asp Tyr Trp Gly Gln Gly
            100                 105                 110

Thr Thr Leu Thr Val Ser Ser
            115
```

<210> SEQ ID NO 27
<211> LENGTH: 119
<212> TYPE: PRT
<213> ORGANISM: Artificial Sequence
<220> FEATURE:
<223> OTHER INFORMATION: OGD201 VH18

<400> SEQUENCE: 27

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Leu Leu Thr Val Ser Ser
            115
```

<210> SEQ ID NO 28
<211> LENGTH: 119
<212> TYPE: PRT
<213> ORGANISM: Artificial Sequence
<220> FEATURE:
<223> OTHER INFORMATION: OGD201 VH19

<400> SEQUENCE: 28

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
```

```
                    50                  55                  60
Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Val Thr Val Ser Ser
        115

<210> SEQ ID NO 29
<211> LENGTH: 112
<212> TYPE: PRT
<213> ORGANISM: Artificial Sequence
<220> FEATURE:
<223> OTHER INFORMATION: OGD201 Consensus sequence for second humanized
      VL sequence
<220> FEATURE:
<221> NAME/KEY: MISC_FEATURE
<222> LOCATION: (1)..(1)
<223> OTHER INFORMATION: X=D or E
<220> FEATURE:
<221> NAME/KEY: MISC_FEATURE
<222> LOCATION: (9)..(9)
<223> OTHER INFORMATION: X=L or A
<220> FEATURE:
<221> NAME/KEY: MISC_FEATURE
<222> LOCATION: (10)..(10)
<223> OTHER INFORMATION: X=S or T
<220> FEATURE:
<221> NAME/KEY: MISC_FEATURE
<222> LOCATION: (12)..(12)
<223> OTHER INFORMATION: X=P or S
<220> FEATURE:
<221> NAME/KEY: MISC_FEATURE
<222> LOCATION: (13)..(13)
<223> OTHER INFORMATION: X=V or L or A
<220> FEATURE:
<221> NAME/KEY: MISC_FEATURE
<222> LOCATION: (14)..(14)
<223> OTHER INFORMATION: X=S or T
<220> FEATURE:
<221> NAME/KEY: MISC_FEATURE
<222> LOCATION: (15)..(15)
<223> OTHER INFORMATION: X=L or P or V
<220> FEATURE:
<221> NAME/KEY: MISC_FEATURE
<222> LOCATION: (17)..(17)
<223> OTHER INFORMATION: X=D or Q or E
<220> FEATURE:
<221> NAME/KEY: MISC_FEATURE
<222> LOCATION: (18)..(18)
<223> OTHER INFORMATION: X=Q or P or R
<220> FEATURE:
<221> NAME/KEY: MISC_FEATURE
<222> LOCATION: (19)..(19)
<223> OTHER INFORMATION: X=A or V
<220> FEATURE:
<221> NAME/KEY: MISC_FEATURE
<222> LOCATION: (20)..(20)
<223> OTHER INFORMATION: X=S or T
<220> FEATURE:
<221> NAME/KEY: MISC_FEATURE
<222> LOCATION: (21)..(21)
<223> OTHER INFORMATION: X=I or L
<220> FEATURE:
<221> NAME/KEY: MISC_FEATURE
<222> LOCATION: (22)..(22)
<223> OTHER INFORMATION: X=S or T
<220> FEATURE:
<221> NAME/KEY: MISC_FEATURE
<222> LOCATION: (25)..(25)
<223> OTHER INFORMATION: X=S or A
<220> FEATURE:
```

```
<221> NAME/KEY: MISC_FEATURE
<222> LOCATION: (29)..(29)
<223> OTHER INFORMATION: X=L or V
<220> FEATURE:
<221> NAME/KEY: MISC_FEATURE
<222> LOCATION: (30)..(30)
<223> OTHER INFORMATION: X=L or V
<220> FEATURE:
<221> NAME/KEY: MISC_FEATURE
<222> LOCATION: (32)..(32)
<223> OTHER INFORMATION: X=N or S
<220> FEATURE:
<221> NAME/KEY: MISC_FEATURE
<222> LOCATION: (33)..(33)
<223> OTHER INFORMATION: X=N or Q or D
<220> FEATURE:
<221> NAME/KEY: MISC_FEATURE
<222> LOCATION: (34)..(34)
<223> OTHER INFORMATION: X=G or A or S
<220> FEATURE:
<221> NAME/KEY: MISC_FEATURE
<222> LOCATION: (35)..(35)
<223> OTHER INFORMATION: X=N or Y or S
<220> FEATURE:
<221> NAME/KEY: MISC_FEATURE
<222> LOCATION: (36)..(36)
<223> OTHER INFORMATION: X=N or T or S
<220> FEATURE:
<221> NAME/KEY: MISC_FEATURE
<222> LOCATION: (37)..(37)
<223> OTHER INFORMATION: X=F or Y
<220> FEATURE:
<221> NAME/KEY: MISC_FEATURE
<222> LOCATION: (39)..(39)
<223> OTHER INFORMATION: X= H or N or S or A or D or Y or G
<220> FEATURE:
<221> NAME/KEY: MISC_FEATURE
<222> LOCATION: (41)..(41)
<223> OTHER INFORMATION: X=Y or F
<220> FEATURE:
<221> NAME/KEY: MISC_FEATURE
<222> LOCATION: (42)..(42)
<223> OTHER INFORMATION: X=L or Q
<220> FEATURE:
<221> NAME/KEY: MISC_FEATURE
<222> LOCATION: (44)..(44)
<223> OTHER INFORMATION: X=K or R
<220> FEATURE:
<221> NAME/KEY: MISC_FEATURE
<222> LOCATION: (47)..(47)
<223> OTHER INFORMATION: X=Q or K
<220> FEATURE:
<221> NAME/KEY: MISC_FEATURE
<222> LOCATION: (48)..(48)
<223> OTHER INFORMATION: X=S or A or V
<220> FEATURE:
<221> NAME/KEY: MISC_FEATURE
<222> LOCATION: (50)..(50)
<223> OTHER INFORMATION: X=K or Q or R
<220> FEATURE:
<221> NAME/KEY: MISC_FEATURE
<222> LOCATION: (51)..(51)
<223> OTHER INFORMATION: X=L or R or V
<220> FEATURE:
<221> NAME/KEY: MISC_FEATURE
<222> LOCATION: (55)..(55)
<223> OTHER INFORMATION: X=K or G or L
<220> FEATURE:
<221> NAME/KEY: MISC_FEATURE
<222> LOCATION: (56)..(56)
<223> OTHER INFORMATION: X= V or A or G
<220> FEATURE:
<221> NAME/KEY: MISC_FEATURE
<222> LOCATION: (58)..(58)
<223> OTHER INFORMATION: X= N or T
<220> FEATURE:
<221> NAME/KEY: MISC_FEATURE
<222> LOCATION: (60)..(60)
<223> OTHER INFORMATION: X= L or D or A
```

```
<220> FEATURE:
<221> NAME/KEY: MISC_FEATURE
<222> LOCATION: (61)..(61)
<223> OTHER INFORMATION: X=S or T
<220> FEATURE:
<221> NAME/KEY: MISC_FEATURE
<222> LOCATION: (63)..(63)
<223> OTHER INFORMATION: X=V or I
<220> FEATURE:
<221> NAME/KEY: MISC_FEATURE
<222> LOCATION: (65)..(65)
<223> OTHER INFORMATION: X=D or A or S
<220> FEATURE:
<221> NAME/KEY: MISC_FEATURE
<222> LOCATION: (75)..(75)
<223> OTHER INFORMATION: X=Y or D
<220> FEATURE:
<221> NAME/KEY: MISC_FEATURE
<222> LOCATION: (79)..(79)
<223> OTHER INFORMATION: X=K or T
<220> FEATURE:
<221> NAME/KEY: MISC_FEATURE
<222> LOCATION: (81)..(81)
<223> OTHER INFORMATION: X=S or N
<220> FEATURE:
<221> NAME/KEY: MISC_FEATURE
<222> LOCATION: (82)..(82)
<223> OTHER INFORMATION: X=R or S
<220> FEATURE:
<221> NAME/KEY: MISC_FEATURE
<222> LOCATION: (83)..(83)
<223> OTHER INFORMATION: X=V or L
<220> FEATURE:
<221> NAME/KEY: MISC_FEATURE
<222> LOCATION: (84)..(84)
<223> OTHER INFORMATION: X=E or Q
<220> FEATURE:
<221> NAME/KEY: MISC_FEATURE
<222> LOCATION: (85)..(85)
<223> OTHER INFORMATION: X=A or P
<220> FEATURE:
<221> NAME/KEY: MISC_FEATURE
<222> LOCATION: (88)..(88)
<223> OTHER INFORMATION: X=L or V or F
<220> FEATURE:
<221> NAME/KEY: MISC_FEATURE
<222> LOCATION: (89)..(89)
<223> OTHER INFORMATION: X=G or A
<220> FEATURE:
<221> NAME/KEY: MISC_FEATURE
<222> LOCATION: (90)..(90)
<223> OTHER INFORMATION: X=V or T
<220> FEATURE:
<221> NAME/KEY: MISC_FEATURE
<222> LOCATION: (92)..(92)
<223> OTHER INFORMATION: X=Y or F
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: X=S or G or A
<220> FEATURE:
<221> NAME/KEY: MISC_FEATURE
<222> LOCATION: (97)..(97)
<223> OTHER INFORMATION: X=T or Y or L
<220> FEATURE:
<221> NAME/KEY: MISC_FEATURE
<222> LOCATION: (98)..(98)
<223> OTHER INFORMATION: X=H or Q or N
<220> FEATURE:
<221> NAME/KEY: MISC_FEATURE
<222> LOCATION: (98)..(98)
<223> OTHER INFORMATION: X=H or Q or N
<220> FEATURE:
<221> NAME/KEY: MISC_FEATURE
<222> LOCATION: (99)..(99)
```

```
<223> OTHER INFORMATION: X= I or W or T
<220> FEATURE:
<221> NAME/KEY: MISC_FEATURE
<222> LOCATION: (100)..(100)
<223> OTHER INFORMATION: X= P or S
<220> FEATURE:
<221> NAME/KEY: MISC_FEATURE
<222> LOCATION: (105)..(105)
<223> OTHER INFORMATION: X=G or Q

<400> SEQUENCE: 29

Xaa Val Val Met Thr Gln Ser Pro Xaa Xaa Leu Xaa Xaa Xaa Xaa Gly
1               5                   10                  15

Xaa Xaa Xaa Xaa Xaa Xaa Cys Arg Xaa Ser Gln Ser Xaa Xaa Lys Xaa
            20                  25                  30

Xaa Xaa Xaa Xaa Xaa Leu Xaa Trp Xaa Xaa Gln Xaa Pro Gly Xaa Xaa
        35                  40                  45

Pro Xaa Xaa Leu Ile Tyr Xaa Xaa Ser Xaa Arg Xaa Xaa Gly Xaa Pro
    50                  55                  60

Xaa Arg Phe Ser Gly Ser Gly Ser Gly Thr Xaa Phe Thr Leu Xaa Ile
65                  70                  75                  80

Xaa Xaa Xaa Xaa Xaa Glu Asp Xaa Xaa Xaa Tyr Xaa Cys Xaa Gln Xaa
                85                  90                  95

Xaa Xaa Xaa Xaa Tyr Thr Phe Gly Xaa Gly Thr Lys Val Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: OGD201 VL5

<400> SEQUENCE: 30

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: OGD201 VL6

<400> SEQUENCE: 31

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Asn
            20                  25                  30
```

```
Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Ile Pro Tyr Thr Phe Gly Gly Gly Thr Lys Leu Glu Ile Lys
                100                 105                 110

<210> SEQ ID NO 32
<211> LENGTH: 112
<212> TYPE: PRT
<213> ORGANISM: Artificial Sequence
<220> FEATURE:
<223> OTHER INFORMATION: OGD201 VL7

<400> SEQUENCE: 32

Asp Val Val Met Thr Gln Thr Pro Leu Ser Leu Pro Val Ser Leu Gly
 1                5                  10                  15

Asp Gln Ala Ser Ile Ser Cys Arg Ser Ser Gln Ser Leu Leu Lys Asn
                 20                  25                  30

Gln Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Ile Pro Tyr Thr Phe Gly Gly Gly Thr Lys Leu Glu Ile Lys
                100                 105                 110

<210> SEQ ID NO 33
<211> LENGTH: 112
<212> TYPE: PRT
<213> ORGANISM: Artificial Sequence
<220> FEATURE:
<223> OTHER INFORMATION: OGD201 VL8

<400> SEQUENCE: 33

Asp Val Val Met Thr Gln Thr Pro Leu Ser Leu Pro Val Ser Leu Gly
 1                5                  10                  15

Asp Gln Ala Ser Ile Ser Cys Arg Ser Ser Gln Ser Leu Leu Lys Asn
                 20                  25                  30

Asn Ala Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Ile Pro Tyr Thr Phe Gly Gly Gly Thr Lys Leu Glu Ile Lys
                100                 105                 110
```

<210> SEQ ID NO 34
<211> LENGTH: 112
<212> TYPE: PRT
<213> ORGANISM: Artificial Sequence
<220> FEATURE:
<223> OTHER INFORMATION: OGD201 VL9

<400> SEQUENCE: 34

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Tyr Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 35
<211> LENGTH: 112
<212> TYPE: PRT
<213> ORGANISM: Artificial Sequence
<220> FEATURE:
<223> OTHER INFORMATION: OGD201 VL10

<400> SEQUENCE: 35

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Phe Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 36
<211> LENGTH: 112
<212> TYPE: PRT
<213> ORGANISM: Artificial Sequence
<220> FEATURE:
<223> OTHER INFORMATION: OGD201 VL11

<400> SEQUENCE: 36

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45
```

```
Pro Lys Arg Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 37
<211> LENGTH: 112
<212> TYPE: PRT
<213> ORGANISM: Artificial Sequence
<220> FEATURE:
<223> OTHER INFORMATION: OGD201 VL12

<400> SEQUENCE: 37

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                20                  25                  30

Asn Gly Asn Thr Phe Leu His Trp Tyr Leu Gln Lys Ser Gly Gln Ser
            35                  40                  45

Pro Lys Val Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: OGD201 VL13

<400> SEQUENCE: 38

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Asn Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 39
<211> LENGTH: 112
<212> TYPE: PRT

-continued

<213> ORGANISM: Artificial Sequence
<220> FEATURE:
<223> OTHER INFORMATION: OGD201 VL14

<400> SEQUENCE: 39

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 40
<211> LENGTH: 119
<212> TYPE: PRT
<213> ORGANISM: Artificial Sequence
<220> FEATURE:
<223> OTHER INFORMATION: OGD201 VH19

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
            20                  25                  30

Tyr Met Thr Trp Val Arg Gln Ala Pro Gly Lys Gly Leu Glu Trp Val
        35                  40                  45

Gly Phe Ile Arg Asn Arg Ala Asn Ala Tyr Thr Thr Glu Tyr Ala Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: OGD201 VH20

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

```
Gly Phe Ile Arg Asn Arg Ala Asn Ala Tyr Thr Thr Glu Tyr Ala Ala
        50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
                100                 105                 110

Thr Leu Val Thr Val Ser Ser
        115

<210> SEQ ID NO 42
<211> LENGTH: 119
<212> TYPE: PRT
<213> ORGANISM: Artificial Sequence
<220> FEATURE:
<223> OTHER INFORMATION: OGD201 VH21

<400> SEQUENCE: 42

Glu Val Gln Leu Val Glu Ser Gly Gly Gly Leu Val Gln Pro Gly Arg
 1               5                  10                  15

Ser Leu Arg Leu Ser Cys Thr Ala Ser Glu Phe Thr Phe Thr Asp Tyr
                20                  25                  30

Tyr Met Thr Trp Val Arg Gln Ala Pro Gly Lys Gly Leu Glu Trp Leu
            35                  40                  45

Gly Phe Ile Arg Asn Arg Ala Asn Ala Tyr Thr Thr Glu Tyr Ala Ala
        50                  55                  60

Ser Val Lys Gly Arg Phe Thr Ile Ser Arg Asp Asn Ser Lys Ser Ile
 65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
                100                 105                 110

Thr Leu Val Thr Val Ser Ser
        115

<210> SEQ ID NO 43
<211> LENGTH: 112
<212> TYPE: PRT
<213> ORGANISM: Artificial Sequence
<220> FEATURE:
<223> OTHER INFORMATION: OGD201 VL15

<400> SEQUENCE: 43

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Lys Asn
                20                  25                  30

Gln Ala Asn Thr Tyr Leu His Trp Phe Gln Gln Arg Pro Gly Gln Ser
            35                  40                  45

Pro Arg Leu Leu Ile Tyr Lys Val Ser Asn Arg Leu Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Ile Pro Tyr Thr Phe Gly Gly Gly Thr Lys Val Glu Ile Lys
```

<210> SEQ ID NO 44
<211> LENGTH: 112
<212> TYPE: PRT
<213> ORGANISM: Artificial Sequence
<220> FEATURE:
<223> OTHER INFORMATION: OGD201 VL16

<400> SEQUENCE: 44

Glu Val Val Met Thr Gln Ser Pro Ala Thr Leu Ser Leu Thr Pro Gly
1               5                   10                  15

Gln Pro Ala Thr Leu Ser Cys Arg Ser Ser Gln Ser Leu Val Lys Asn
            20                  25                  30

Gln Ala Asn Thr Tyr Leu His Trp Phe Gln Gln Arg Pro Gly Gln Ala
        35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Gln Pro Glu Asp Val Ala Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: OGD201 VL17

<400> SEQUENCE: 45

Glu Val Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Val Lys Asn
            20                  25                  30

Gln Ala Asn Thr Tyr Leu His Trp Tyr Gln Gln Lys Pro Gly Gln Ala
        35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Gln Ala Glu Asp Phe Ala Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: OGD201 VL18

<400> SEQUENCE: 46

Glu Val Val Met Thr Gln Ser Pro Ala Thr Leu Ser Leu Thr Pro Gly
1               5                   10                  15

Glu Arg Ala Thr Leu Ser Cys Arg Ser Ser Gln Ser Leu Val Lys Asn
            20                  25                  30

Gln Ala Asn Thr Tyr Leu His Trp Phe Gln Gln Arg Pro Gly Gln Ala
         35                  40                  45

Pro Arg Leu Leu Ile Tyr Lys Val Ser Asn Arg Leu Thr Gly Ile Pro
 50                  55                  60

Ala Arg Phe Ser Gly Ser Gly Ser Gly Thr Asp Phe Thr Leu Thr Ile
 65                  70                  75                  80

Ser Ser Leu Gln Pro Glu Asp Phe Ala Val Tyr Tyr Cys Ser Gln Ser
                 85                  90                  95

Thr His Ile Pro Tyr Thr Phe Gly Gly Gly Thr Lys Val Glu Ile Lys
                 100                 105                 110

<210> SEQ ID NO 47
<211> LENGTH: 119
<212> TYPE: PRT
<213> ORGANISM: Artificial Sequence
<220> FEATURE:
<223> OTHER INFORMATION: OGD201 VH22

<400> SEQUENCE: 47

Glu Val Lys Leu Val Glu Ser Gly Gly Gly Leu Val Leu Pro Gly Asp
1                5                  10                  15

Ser Leu Arg Leu Ser Cys Ala Thr Ser Gly Phe Thr Phe Thr Asp Tyr
                 20                  25                  30

Tyr Met Thr Trp Val Arg Gln Pro Pro Arg Lys Ala Leu Glu Trp Leu
         35                  40                  45

Gly Phe Ile Arg Asn Arg Ala Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
                 100                 105                 110

Thr Thr Leu Thr Val Ser Ser
         115

<210> SEQ ID NO 48
<211> LENGTH: 119
<212> TYPE: PRT
<213> ORGANISM: Artificial Sequence
<220> FEATURE:
<223> OTHER INFORMATION: OGD201 VH23

<400> SEQUENCE: 48

Glu Val Lys Leu Val Glu Ser Gly Gly Gly Leu Val Leu Pro Gly Asp
1                5                  10                  15

Ser Leu Arg Leu Ser Cys Ala Thr Ser Glu Phe Thr Ser Thr Asp Tyr
                 20                  25                  30

Tyr Met Thr Trp Val Arg Gln Pro Pro Arg Lys Ala Leu Glu Trp Leu
         35                  40                  45

Gly Phe Ile Arg Asn Arg Ala Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly

```
                   100                 105                 110
Thr Thr Leu Thr Val Ser Ser
            115

<210> SEQ ID NO 49
<211> LENGTH: 119
<212> TYPE: PRT
<213> ORGANISM: Artificial Sequence
<220> FEATURE:
<223> OTHER INFORMATION: OGD201 VH24

<400> SEQUENCE: 49

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Ser Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 50
<211> LENGTH: 119
<212> TYPE: PRT
<213> ORGANISM: Artificial Sequence
<220> FEATURE:
<223> OTHER INFORMATION: OGD201 VH25

<400> SEQUENCE: 50

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp His
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 51
<211> LENGTH: 119
<212> TYPE: PRT
<213> ORGANISM: Artificial Sequence
<220> FEATURE:
```

<223> OTHER INFORMATION: OGD201 VH26

<400> SEQUENCE: 51

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Ala Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: OGD201 VH27

<400> SEQUENCE: 52

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Asp Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: OGD201 VH28

<400> SEQUENCE: 53

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Ser Trp Val Arg Gln Pro Pro Arg Lys Ala Leu Glu Trp Leu

```
                35                  40                  45
Gly Phe Ile Arg Asn Arg Ala Asn Gly Tyr Thr Thr Glu Tyr Asn Pro
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115

<210> SEQ ID NO 54
<211> LENGTH: 119
<212> TYPE: PRT
<213> ORGANISM: Artificial Sequence
<220> FEATURE:
<223> OTHER INFORMATION: OGD201 VH29

<400> SEQUENCE: 54

Glu Val Lys Leu Val Glu Ser Gly Gly Gly Leu Val Leu Pro Gly Asp
  1               5                  10                  15

Ser Leu Arg Leu Ser Cys Ala Thr Ser Glu Phe Thr Phe Thr Asp Tyr
                 20                  25                  30

Tyr Met His Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115

<210> SEQ ID NO 55
<211> LENGTH: 119
<212> TYPE: PRT
<213> ORGANISM: Artificial Sequence
<220> FEATURE:
<223> OTHER INFORMATION: OGD201 VH30

<400> SEQUENCE: 55

Glu Val Lys Leu Val Glu Ser Gly Gly Gly Leu Val Leu Pro Gly Asp
  1               5                  10                  15

Ser Leu Arg Leu Ser Cys Ala Thr Ser Glu Phe Thr Phe Thr Asp Tyr
                 20                  25                  30

Tyr Met Asn Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
         50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95
```

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 56
<211> LENGTH: 119
<212> TYPE: PRT
<213> ORGANISM: Artificial Sequence
<220> FEATURE:
<223> OTHER INFORMATION: OGD201 VH31

<400> SEQUENCE: 56

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Arg Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: OGD201 VH32

<400> SEQUENCE: 57

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Tyr Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 58
<211> LENGTH: 119
<212> TYPE: PRT
<213> ORGANISM: Artificial Sequence -continued

```
<220> FEATURE:
<223> OTHER INFORMATION: OGD201 VH33

<400> SEQUENCE: 58

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Thr Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: OGD201 VH34

<400> SEQUENCE: 59

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Ser Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: OGD201 VH35

<400> SEQUENCE: 60

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30
```

Tyr Met Thr Trp Val Arg Gln Pro Pro Arg Lys Ala Leu Glu Trp Leu
            35                  40                  45

Gly Phe Ile Arg Asn Lys Ala Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
                 100                 105                 110

Thr Thr Leu Thr Val Ser Ser
        115

<210> SEQ ID NO 61
<211> LENGTH: 119
<212> TYPE: PRT
<213> ORGANISM: Artificial Sequence
<220> FEATURE:
<223> OTHER INFORMATION: OGD201 VH36

<400> SEQUENCE: 61

Glu Val Lys Leu Val Glu Ser Gly Gly Gly Leu Val Leu Pro Gly Asp
 1               5                  10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Ser Ala Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
                 100                 105                 110

Thr Thr Leu Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: OGD201 VH37

<400> SEQUENCE: 62

Glu Val Lys Leu Val Glu Ser Gly Gly Gly Leu Val Leu Pro Gly Asp
 1               5                  10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ser Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                85                  90                  95

-continued

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: OGD201 VH38

<400> SEQUENCE: 63

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Tyr Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: OGD201 VH39

<400> SEQUENCE: 64

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Ser Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 65
<211> LENGTH: 119
<212> TYPE: PRT

<213> ORGANISM: Artificial Sequence
<220> FEATURE:
<223> OTHER INFORMATION: OGD201 VH40

<400> SEQUENCE: 65

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Ser Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: OGD201 VH41

<400> SEQUENCE: 66

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Gly Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: OGD201 VH42

<400> SEQUENCE: 67

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

```
Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Tyr Tyr Asn Pro
            50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                    85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115
```

<210> SEQ ID NO 68
<211> LENGTH: 119
<212> TYPE: PRT
<213> ORGANISM: Artificial Sequence
<220> FEATURE:
<223> OTHER INFORMATION: OGD201 VH43

<400> SEQUENCE: 68

```
Glu Val Lys Leu Val Glu Ser Gly Gly Gly Leu Val Leu Pro Gly Asp
 1               5                  10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
            50                  55                  60

Ser Val Lys Gly Arg Phe Thr Ile Ser Arg Asp Gly Ser Gln Ser Ile
 65                  70                  75                  80

Leu Tyr Leu Gln Met Asn Thr Leu Arg Thr Glu Asp Ser Ala Thr Tyr
                    85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115
```

<210> SEQ ID NO 69
<211> LENGTH: 119
<212> TYPE: PRT
<213> ORGANISM: Artificial Sequence
<220> FEATURE:
<223> OTHER INFORMATION: OGD201 VH44

<400> SEQUENCE: 69

```
Glu Val Lys Leu Val Glu Ser Gly Gly Gly Leu Val Leu Pro Gly Asp
 1               5                  10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
            50                  55                  60

Ser Val Lys Gly Arg Phe Thr Ile Ser Arg Asp Asn Ala Gln Ser Ile
 65                  70                  75                  80

Leu Tyr Leu Gln Met Asn Thr Leu Arg Thr Glu Asp Ser Ala Thr Tyr
```

-continued

```
                    85                  90                  95

Tyr Cys Ala Arg Val Ser Asn Trp Ala Phe Asp Tyr Trp Gln Gly
                100                 105                 110

Thr Thr Leu Thr Val Ser Ser
            115

<210> SEQ ID NO 70
<211> LENGTH: 119
<212> TYPE: PRT
<213> ORGANISM: Artificial Sequence
<220> FEATURE:
<223> OTHER INFORMATION: OGD201 VH45

<400> SEQUENCE: 70

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Ala Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115

<210> SEQ ID NO 71
<211> LENGTH: 119
<212> TYPE: PRT
<213> ORGANISM: Artificial Sequence
<220> FEATURE:
<223> OTHER INFORMATION: OGD201 VH46

<400> SEQUENCE: 71

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Val Ser Asn Trp Ala Phe Asp Tyr Trp Gly Gln Gly
                100                 105                 110

Thr Thr Leu Thr Val Ser Ser
            115

<210> SEQ ID NO 72
<211> LENGTH: 119
```

```
<212> TYPE: PRT
<213> ORGANISM: Artificial Sequence
<220> FEATURE:
<223> OTHER INFORMATION: OGD201 VH47

<400> SEQUENCE: 72
```

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Leu Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

```
<210> SEQ ID NO 73
<211> LENGTH: 119
<212> TYPE: PRT
<213> ORGANISM: Artificial Sequence
<220> FEATURE:
<223> OTHER INFORMATION: OGD201 VH48

<400> SEQUENCE: 73
```

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Thr Arg Val Ser Asn Trp Ala Phe Asp Tyr Trp Gly Gln Gly
            100                 105                 110

Thr Thr Leu Thr Val Ser Ser
        115

```
<210> SEQ ID NO 74
<211> LENGTH: 119
<212> TYPE: PRT
<213> ORGANISM: Artificial Sequence
<220> FEATURE:
<223> OTHER INFORMATION: OGD201 VH49

<400> SEQUENCE: 74
```

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr

```
                    20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Tyr Ala Phe Asp Tyr Trp Gly Gln Gly
            100                 105                 110

Thr Thr Leu Thr Val Ser Ser
        115

<210> SEQ ID NO 75
<211> LENGTH: 119
<212> TYPE: PRT
<213> ORGANISM: Artificial Sequence
<220> FEATURE:
<223> OTHER INFORMATION: OGD201 VH50

<400> SEQUENCE: 75

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Tyr Phe Asp Tyr Trp Gly Gln Gly
            100                 105                 110

Thr Thr Leu Thr Val Ser Ser
        115

<210> SEQ ID NO 76
<211> LENGTH: 119
<212> TYPE: PRT
<213> ORGANISM: Artificial Sequence
<220> FEATURE:
<223> OTHER INFORMATION: OGD201 Consensus sequence for third humanized
      VH sequence
<220> FEATURE:
<221> NAME/KEY: MISC_FEATURE
<222> LOCATION: (1)..(1)
<223> OTHER INFORMATION: X=E or Q
<220> FEATURE:
<221> NAME/KEY: MISC_FEATURE
<222> LOCATION: (5)..(5)
<223> OTHER INFORMATION: X=V or L
<220> FEATURE:
<221> NAME/KEY: MISC_FEATURE
<222> LOCATION: (13)..(13)
<223> OTHER INFORMATION: X=Q or K
<220> FEATURE:
<221> NAME/KEY: MISC_FEATURE
<222> LOCATION: (16)..(16)
<223> OTHER INFORMATION: X= G or R
<220> FEATURE:
```

```
<221> NAME/KEY: MISC_FEATURE
<222> LOCATION: (23)..(23)
<223> OTHER INFORMATION: X= A or T
<220> FEATURE:
<221> NAME/KEY: MISC_FEATURE
<222> LOCATION: (24)..(24)
<223> OTHER INFORMATION: X= T or A
<220> FEATURE:
<221> NAME/KEY: MISC_FEATURE
<222> LOCATION: (26)..(26)
<223> OTHER INFORMATION: X= E or G
<220> FEATURE:
<221> NAME/KEY: MISC_FEATURE
<222> LOCATION: (30)..(30)
<223> OTHER INFORMATION: X= T or S or G
<220> FEATURE:
<221> NAME/KEY: MISC_FEATURE
<222> LOCATION: (32)..(32)
<223> OTHER INFORMATION: X= Y or H
<220> FEATURE:
<221> NAME/KEY: MISC_FEATURE
<222> LOCATION: (35)..(35)
<223> OTHER INFORMATION: X= T or D or S or H or N
<220> FEATURE:
<221> NAME/KEY: MISC_FEATURE
<222> LOCATION: (48)..(48)
<223> OTHER INFORMATION: X= L or V
<220> FEATURE:
<221> NAME/KEY: MISC_FEATURE
<222> LOCATION: (49)..(49)
<223> OTHER INFORMATION: X= G or S
<220> FEATURE:
<221> NAME/KEY: MISC_FEATURE
<222> LOCATION: (50)..(50)
<223> OTHER INFORMATION: X= F or Y
<220> FEATURE:
<221> NAME/KEY: MISC_FEATURE
<222> LOCATION: (51)..(51)
<223> OTHER INFORMATION: X= I or T
<220> FEATURE:
<221> NAME/KEY: MISC_FEATURE
<222> LOCATION: (54)..(54)
<223> OTHER INFORMATION: X= R or K or S
<220> FEATURE:
<221> NAME/KEY: MISC_FEATURE
<222> LOCATION: (55)..(55)
<223> OTHER INFORMATION: X= A or S
<220> FEATURE:
<221> NAME/KEY: MISC_FEATURE
<222> LOCATION: (57)..(57)
<223> OTHER INFORMATION: X= G or A or S
<220> FEATURE:
<221> NAME/KEY: MISC_FEATURE
<222> LOCATION: (58)..(58)
<223> OTHER INFORMATION: X= Y or S or G
<220> FEATURE:
<221> NAME/KEY: MISC_FEATURE
<222> LOCATION: (59)..(59)
<223> OTHER INFORMATION: X= T or I
<220> FEATURE:
<221> NAME/KEY: MISC_FEATURE
<222> LOCATION: (60)..(60)
<223> OTHER INFORMATION: X= T or I
<220> FEATURE:
<221> NAME/KEY: MISC_FEATURE
<222> LOCATION: (61)..(61)
<223> OTHER INFORMATION: X= E or Y
<220> FEATURE:
<221> NAME/KEY: MISC_FEATURE
<222> LOCATION: (63)..(63)
<223> OTHER INFORMATION: X= N or A
<220> FEATURE:
<221> NAME/KEY: MISC_FEATURE
<222> LOCATION: (64)..(64)
<223> OTHER INFORMATION: X= P or A or D
<220> FEATURE:
<221> NAME/KEY: MISC_FEATURE
<222> LOCATION: (76)..(76)
<223> OTHER INFORMATION: X= N or G
```

```
<220> FEATURE:
<221> NAME/KEY: MISC_FEATURE
<222> LOCATION: (77)..(77)
<223> OTHER INFORMATION: X= S or A
<220> FEATURE:
<221> NAME/KEY: MISC_FEATURE
<222> LOCATION: (79)..(79)
<223> OTHER INFORMATION: X= S or N
<220> FEATURE:
<221> NAME/KEY: MISC_FEATURE
<222> LOCATION: (80)..(80)
<223> OTHER INFORMATION: X= I or S or T
<220> FEATURE:
<221> NAME/KEY: MISC_FEATURE
<222> LOCATION: (81)..(81)
<223> OTHER INFORMATION: X= L or T or A
<220> FEATURE:
<221> NAME/KEY: MISC_FEATURE
<222> LOCATION: (89)..(89)
<223> OTHER INFORMATION: X= R or K or Q
<220> FEATURE:
<221> NAME/KEY: MISC_FEATURE
<222> LOCATION: (90)..(90)
<223> OTHER INFORMATION: X= T or A
<220> FEATURE:
<221> NAME/KEY: MISC_FEATURE
<222> LOCATION: (95)..(95)
<223> OTHER INFORMATION: X= V or I or L
<220> FEATURE:
<221> NAME/KEY: MISC_FEATURE
<222> LOCATION: (99)..(99)
<223> OTHER INFORMATION: X= T or A
<220> FEATURE:
<221> NAME/KEY: MISC_FEATURE
<222> LOCATION: (114)..(114)
<223> OTHER INFORMATION: X= T or L
<220> FEATURE:
<221> NAME/KEY: MISC_FEATURE
<222> LOCATION: (115)..(115)
<223> OTHER INFORMATION: X= L or V

<400> SEQUENCE: 76

Xaa Val Gln Leu Xaa Glu Ser Gly Gly Gly Leu Val Xaa Pro Gly Xaa
1               5                   10                  15

Ser Leu Arg Leu Ser Cys Xaa Xaa Ser Xaa Phe Thr Phe Xaa Asp Xaa
            20                  25                  30

Tyr Met Xaa Trp Val Arg Gln Ala Pro Gly Lys Gly Leu Glu Trp Xaa
        35                  40                  45

Xaa Xaa Xaa Arg Asn Xaa Xaa Asn Xaa Xaa Xaa Xaa Xaa Tyr Xaa Xaa
    50                  55                  60

Ser Val Lys Gly Arg Phe Thr Ile Ser Arg Asp Xaa Xaa Lys Xaa Xaa
65                  70                  75                  80

Xaa Tyr Leu Gln Met Asn Ser Leu Xaa Xaa Glu Asp Thr Ala Xaa Tyr
                85                  90                  95

Tyr Cys Xaa Arg Val Ser Asn Trp Ala Phe Asp Tyr Trp Gly Gln Gly
            100                 105                 110

Thr Xaa Xaa Thr Val Ser Ser
        115

<210> SEQ ID NO 77
<211> LENGTH: 112
<212> TYPE: PRT
<213> ORGANISM: Artificial Sequence
<220> FEATURE:
<223> OTHER INFORMATION: OGD201 VL19

<400> SEQUENCE: 77

Asp Val Val Met Thr Gln Thr Pro Leu Ser Leu Pro Val Ser Leu Gly
1               5                   10                  15
```

Asp Gln Ala Ser Ile Ser Cys Arg Ala Ser Gln Ser Leu Leu Lys Asn
                20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
                100                 105                 110

<210> SEQ ID NO 78
<211> LENGTH: 112
<212> TYPE: PRT
<213> ORGANISM: Artificial Sequence
<220> FEATURE:
<223> OTHER INFORMATION: OGD201 VL20

<400> SEQUENCE: 78

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Val Leu Lys Asn
                20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
                100                 105                 110

<210> SEQ ID NO 79
<211> LENGTH: 112
<212> TYPE: PRT
<213> ORGANISM: Artificial Sequence
<220> FEATURE:
<223> OTHER INFORMATION: OGD201 VL21

<400> SEQUENCE: 79

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Ser
                20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys

<210> SEQ ID NO 80
<211> LENGTH: 112
<212> TYPE: PRT
<213> ORGANISM: Artificial Sequence
<220> FEATURE:
<223> OTHER INFORMATION: OGD201 VL22

<400> SEQUENCE: 80

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asp Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 81
<211> LENGTH: 112
<212> TYPE: PRT
<213> ORGANISM: Artificial Sequence
<220> FEATURE:
<223> OTHER INFORMATION: OGD201 VL23

<400> SEQUENCE: 81

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Ser Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: OGD201 VL24

<400> SEQUENCE: 82

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Tyr Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
               100                 105                 110

<210> SEQ ID NO 83
<211> LENGTH: 112
<212> TYPE: PRT
<213> ORGANISM: Artificial Sequence
<220> FEATURE:
<223> OTHER INFORMATION: OGD201 VL25

<400> SEQUENCE: 83

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Ser Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
               100                 105                 110

<210> SEQ ID NO 84
<211> LENGTH: 112
<212> TYPE: PRT
<213> ORGANISM: Artificial Sequence
<220> FEATURE:
<223> OTHER INFORMATION: OGD201 VL26

<400> SEQUENCE: 84

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Asn Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
               100                 105                 110

```
<210> SEQ ID NO 85
<211> LENGTH: 112
<212> TYPE: PRT
<213> ORGANISM: Artificial Sequence
<220> FEATURE:
<223> OTHER INFORMATION: OGD201 VL27

<400> SEQUENCE: 85

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Ser Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 86
<211> LENGTH: 112
<212> TYPE: PRT
<213> ORGANISM: Artificial Sequence
<220> FEATURE:
<223> OTHER INFORMATION: OGD201 VL28

<400> SEQUENCE: 86

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu Asn Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 87
<211> LENGTH: 112
<212> TYPE: PRT
<213> ORGANISM: Artificial Sequence
<220> FEATURE:
<223> OTHER INFORMATION: OGD201 VL29

<400> SEQUENCE: 87

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu Ser Trp Tyr Leu Gln Lys Ser Gly Gln Ser
        35                  40                  45
```

```
Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
 65              70                  75                      80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 88
<211> LENGTH: 112
<212> TYPE: PRT
<213> ORGANISM: Artificial Sequence
<220> FEATURE:
<223> OTHER INFORMATION: OGD201 VL30

<400> SEQUENCE: 88

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Leu Lys Asn
            20                  25                  30

Asn Gly Asn Thr Phe Leu Ala Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
 65              70                  75                      80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 89
<211> LENGTH: 112
<212> TYPE: PRT
<213> ORGANISM: Artificial Sequence
<220> FEATURE:
<223> OTHER INFORMATION: OGD201 VL31

<400> SEQUENCE: 89

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Leu Lys Asn
            20                  25                  30

Asn Gly Asn Thr Phe Leu Asp Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
 65              70                  75                      80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 90
<211> LENGTH: 112
<212> TYPE: PRT

```
<213> ORGANISM: Artificial Sequence
<220> FEATURE:
<223> OTHER INFORMATION: OGD201 VL32

<400> SEQUENCE: 90

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu Tyr Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
                100                 105                 110

<210> SEQ ID NO 91
<211> LENGTH: 112
<212> TYPE: PRT
<213> ORGANISM: Artificial Sequence
<220> FEATURE:
<223> OTHER INFORMATION: OGD201 VL33

<400> SEQUENCE: 91

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu Gly Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
                100                 105                 110

<210> SEQ ID NO 92
<211> LENGTH: 112
<212> TYPE: PRT
<213> ORGANISM: Artificial Sequence
<220> FEATURE:
<223> OTHER INFORMATION: OGD201 VL34

<400> SEQUENCE: 92

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ala
        35                  40                  45

Pro Lys Leu Leu Ile Tyr Lys Val Ser Asn Arg Leu Ser Gly Val Pro
    50                  55                  60
```

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 93
<211> LENGTH: 112
<212> TYPE: PRT
<213> ORGANISM: Artificial Sequence
<220> FEATURE:
<223> OTHER INFORMATION: OGD201 VL35

<400> SEQUENCE: 93

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Val
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: OGD201 VL36

<400> SEQUENCE: 94

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Gly Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 95
<211> LENGTH: 112
<212> TYPE: PRT
<213> ORGANISM: Artificial Sequence
<220> FEATURE:
<223> OTHER INFORMATION: OGD201 VL37

<400> SEQUENCE: 95

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Leu Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 96
<211> LENGTH: 112
<212> TYPE: PRT
<213> ORGANISM: Artificial Sequence
<220> FEATURE:
<223> OTHER INFORMATION: OGD201 VL38

<400> SEQUENCE: 96

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Ala Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 97
<211> LENGTH: 112
<212> TYPE: PRT
<213> ORGANISM: Artificial Sequence
<220> FEATURE:
<223> OTHER INFORMATION: OGD201 VL39

<400> SEQUENCE: 97

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Gly Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
            85                  90                  95

Thr His Ile Pro Tyr Thr Phe Gly Gly Gly Thr Lys Leu Glu Ile Lys
            100                 105                 110

<210> SEQ ID NO 98
<211> LENGTH: 112
<212> TYPE: PRT
<213> ORGANISM: Artificial Sequence
<220> FEATURE:
<223> OTHER INFORMATION: OGD201 VL40

<400> SEQUENCE: 98

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Thr Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
            85                  90                  95

Thr His Ile Pro Tyr Thr Phe Gly Gly Gly Thr Lys Leu Glu Ile Lys
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: OGD201 VL41

<400> SEQUENCE: 99

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Ala Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
            85                  90                  95

Thr His Ile Pro Tyr Thr Phe Gly Gly Gly Thr Lys Leu Glu Ile Lys
            100                 105                 110

<210> SEQ ID NO 100
<211> LENGTH: 112
<212> TYPE: PRT
<213> ORGANISM: Artificial Sequence
<220> FEATURE:
<223> OTHER INFORMATION: OGD201 VL42

<400> SEQUENCE: 100

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Asp Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
            85                  90                  95

Thr His Ile Pro Tyr Thr Phe Gly Gly Gly Thr Lys Leu Glu Ile Lys
            100                 105                 110

<210> SEQ ID NO 101
<211> LENGTH: 112
<212> TYPE: PRT
<213> ORGANISM: Artificial Sequence
<220> FEATURE:
<223> OTHER INFORMATION: OGD201 VL43

<400> SEQUENCE: 101

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Gln Gln Ser
            85                  90                  95

Thr His Ile Pro Tyr Thr Phe Gly Gly Gly Thr Lys Leu Glu Ile Lys
            100                 105                 110

<210> SEQ ID NO 102
<211> LENGTH: 112
<212> TYPE: PRT
<213> ORGANISM: Artificial Sequence
<220> FEATURE:
<223> OTHER INFORMATION: OGD201 VL44

<400> SEQUENCE: 102

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Met Gln Ser
            85                  90                  95

Thr His Ile Pro Tyr Thr Phe Gly Gly Gly Thr Lys Leu Glu Ile Lys
            100                 105                 110

<210> SEQ ID NO 103
<211> LENGTH: 112
<212> TYPE: PRT
<213> ORGANISM: Artificial Sequence
<220> FEATURE:
<223> OTHER INFORMATION: OGD201 VL45

<400> SEQUENCE: 103

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ala
                85                  90                  95

Thr His Ile Pro Tyr Thr Phe Gly Gly Gly Thr Lys Leu Glu Ile Lys
            100                 105                 110

<210> SEQ ID NO 104
<211> LENGTH: 112
<212> TYPE: PRT
<213> ORGANISM: Artificial Sequence
<220> FEATURE:
<223> OTHER INFORMATION: OGD201 VL46

<400> SEQUENCE: 104

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Gly
                85                  90                  95

Thr His Ile Pro Tyr Thr Phe Gly Gly Gly Thr Lys Leu Glu Ile Lys
            100                 105                 110

<210> SEQ ID NO 105
<211> LENGTH: 112
<212> TYPE: PRT
<213> ORGANISM: Artificial Sequence
<220> FEATURE:
<223> OTHER INFORMATION: OGD201 VL47

<400> SEQUENCE: 105

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                    20                  25                  30

Asn Gly Asn Thr Phe Leu His Trp Tyr Leu Gln Lys Ser Gly Gln Ser
                35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Tyr His Ile Pro Tyr Thr Phe Gly Gly Gly Thr Lys Leu Glu Ile Lys
                100                 105                 110

<210> SEQ ID NO 106
<211> LENGTH: 112
<212> TYPE: PRT
<213> ORGANISM: Artificial Sequence
<220> FEATURE:
<223> OTHER INFORMATION: OGD201 VL48

<400> SEQUENCE: 106

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                    20                  25                  30

Asn Gly Asn Thr Phe Leu His Trp Tyr Leu Gln Lys Ser Gly Gln Ser
                35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Leu His Ile Pro Tyr Thr Phe Gly Gly Gly Thr Lys Leu Glu Ile Lys
                100                 105                 110

<210> SEQ ID NO 107
<211> LENGTH: 112
<212> TYPE: PRT
<213> ORGANISM: Artificial Sequence
<220> FEATURE:
<223> OTHER INFORMATION: OGD201 VL49

<400> SEQUENCE: 107

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
                    20                  25                  30

Asn Gly Asn Thr Phe Leu His Trp Tyr Leu Gln Lys Ser Gly Gln Ser
                35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr Gln Ile Pro Tyr Thr Phe Gly Gly Gly Thr Lys Leu Glu Ile Lys
                100                 105                 110

<210> SEQ ID NO 108
<211> LENGTH: 112
<212> TYPE: PRT
<213> ORGANISM: Artificial Sequence
<220> FEATURE:
<223> OTHER INFORMATION: OGD201 VL50

<400> SEQUENCE: 108

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr Asn Ile Pro Tyr Thr Phe Gly Gly Gly Thr Lys Leu Glu Ile Lys
            100                 105                 110

<210> SEQ ID NO 109
<211> LENGTH: 112
<212> TYPE: PRT
<213> ORGANISM: Artificial Sequence
<220> FEATURE:
<223> OTHER INFORMATION: OGD201 VL51

<400> SEQUENCE: 109

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Thr Pro Tyr Thr Phe Gly Gly Gly Thr Lys Leu Glu Ile Lys
            100                 105                 110

<210> SEQ ID NO 110
<211> LENGTH: 112
<212> TYPE: PRT
<213> ORGANISM: Artificial Sequence
<220> FEATURE:
<223> OTHER INFORMATION: OGD201 VL52

<400> SEQUENCE: 110

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

```
Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65              70                  75                      80

Ser Arg Val Glu Ala Glu Asp Leu Gly Val Tyr Phe Cys Gln Ser
            85                  90                  95

Thr His Trp Pro Tyr Thr Phe Gly Gly Gly Thr Lys Leu Glu Ile Lys
            100                 105                 110
```

<210> SEQ ID NO 111
<211> LENGTH: 112
<212> TYPE: PRT
<213> ORGANISM: Artificial Sequence
<220> FEATURE:
<223> OTHER INFORMATION: OGD201 VL53

<400> SEQUENCE: 111

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65              70                  75                      80

Ser Arg Val Glu Ala Glu Asp Leu Gly Val Tyr Phe Cys Gln Ser
            85                  90                  95

Thr His Ile Ser Tyr Thr Phe Gly Gly Gly Thr Lys Leu Glu Ile Lys
            100                 105                 110
```

<210> SEQ ID NO 112
<211> LENGTH: 113
<212> TYPE: PRT
<213> ORGANISM: Artificial Sequence
<220> FEATURE:
<223> OTHER INFORMATION: OGD201 Consensus sequence for third humanized
      VL sequence
<220> FEATURE:
<221> NAME/KEY: MISC_FEATURE
<222> LOCATION: (1)..(1)
<223> OTHER INFORMATION: X=D or E
<220> FEATURE:
<221> NAME/KEY: MISC_FEATURE
<222> LOCATION: (9)..(9)
<223> OTHER INFORMATION: X=L or A
<220> FEATURE:
<221> NAME/KEY: MISC_FEATURE
<222> LOCATION: (10)..(10)
<223> OTHER INFORMATION: X=S or T
<220> FEATURE:
<221> NAME/KEY: MISC_FEATURE
<222> LOCATION: (12)..(12)
<223> OTHER INFORMATION: X=P or S
<220> FEATURE:
<221> NAME/KEY: MISC_FEATURE
<222> LOCATION: (13)..(13)
<223> OTHER INFORMATION: X=V or L or A
<220> FEATURE:
<221> NAME/KEY: MISC_FEATURE
<222> LOCATION: (14)..(14)
<223> OTHER INFORMATION: X=S or T
<220> FEATURE:

```
<221> NAME/KEY: MISC_FEATURE
<222> LOCATION: (15)..(15)
<223> OTHER INFORMATION: X=L or P or V
<220> FEATURE:
<221> NAME/KEY: MISC_FEATURE
<222> LOCATION: (17)..(17)
<223> OTHER INFORMATION: X=D or Q or E
<220> FEATURE:
<221> NAME/KEY: MISC_FEATURE
<222> LOCATION: (18)..(18)
<223> OTHER INFORMATION: X=Q or P or R
<220> FEATURE:
<221> NAME/KEY: MISC_FEATURE
<222> LOCATION: (19)..(19)
<223> OTHER INFORMATION: X=A or V
<220> FEATURE:
<221> NAME/KEY: MISC_FEATURE
<222> LOCATION: (20)..(20)
<223> OTHER INFORMATION: X=S or T
<220> FEATURE:
<221> NAME/KEY: MISC_FEATURE
<222> LOCATION: (21)..(21)
<223> OTHER INFORMATION: X=I or L
<220> FEATURE:
<221> NAME/KEY: MISC_FEATURE
<222> LOCATION: (22)..(22)
<223> OTHER INFORMATION: X=S or T
<220> FEATURE:
<221> NAME/KEY: MISC_FEATURE
<222> LOCATION: (25)..(25)
<223> OTHER INFORMATION: X=S or A
<220> FEATURE:
<221> NAME/KEY: MISC_FEATURE
<222> LOCATION: (29)..(29)
<223> OTHER INFORMATION: X=L or V
<220> FEATURE:
<221> NAME/KEY: MISC_FEATURE
<222> LOCATION: (30)..(30)
<223> OTHER INFORMATION: X=L or V
<220> FEATURE:
<221> NAME/KEY: MISC_FEATURE
<222> LOCATION: (32)..(32)
<223> OTHER INFORMATION: X=N or S
<220> FEATURE:
<221> NAME/KEY: MISC_FEATURE
<222> LOCATION: (33)..(33)
<223> OTHER INFORMATION: X=N or Q
<220> FEATURE:
<221> NAME/KEY: MISC_FEATURE
<222> LOCATION: (34)..(34)
<223> OTHER INFORMATION: X=G or A or S
<220> FEATURE:
<221> NAME/KEY: MISC_FEATURE
<222> LOCATION: (35)..(35)
<223> OTHER INFORMATION: X=N or Y or S
<220> FEATURE:
<221> NAME/KEY: MISC_FEATURE
<222> LOCATION: (36)..(36)
<223> OTHER INFORMATION: X=T or N or S
<220> FEATURE:
<221> NAME/KEY: MISC_FEATURE
<222> LOCATION: (37)..(37)
<223> OTHER INFORMATION: X=F or Y
<220> FEATURE:
<221> NAME/KEY: MISC_FEATURE
<222> LOCATION: (39)..(39)
<223> OTHER INFORMATION: X= H or N or S or A or D or Y or G
<220> FEATURE:
<221> NAME/KEY: MISC_FEATURE
<222> LOCATION: (41)..(41)
<223> OTHER INFORMATION: X=Y or F
<220> FEATURE:
<221> NAME/KEY: MISC_FEATURE
<222> LOCATION: (42)..(42)
<223> OTHER INFORMATION: X=L or Q
<220> FEATURE:
<221> NAME/KEY: MISC_FEATURE
<222> LOCATION: (44)..(44)
<223> OTHER INFORMATION: X=K or R
```

-continued

```
<220> FEATURE:
<221> NAME/KEY: MISC_FEATURE
<222> LOCATION: (47)..(47)
<223> OTHER INFORMATION: X=Q or K
<220> FEATURE:
<221> NAME/KEY: MISC_FEATURE
<222> LOCATION: (48)..(48)
<223> OTHER INFORMATION: X=S or A
<220> FEATURE:
<221> NAME/KEY: MISC_FEATURE
<222> LOCATION: (50)..(50)
<223> OTHER INFORMATION: X=K or Q or R
<220> FEATURE:
<221> NAME/KEY: MISC_FEATURE
<222> LOCATION: (51)..(51)
<223> OTHER INFORMATION: X=L or R
<220> FEATURE:
<221> NAME/KEY: MISC_FEATURE
<222> LOCATION: (55)..(55)
<223> OTHER INFORMATION: X=K or G or L
<220> FEATURE:
<221> NAME/KEY: MISC_FEATURE
<222> LOCATION: (56)..(56)
<223> OTHER INFORMATION: X=V or A or G
<220> FEATURE:
<221> NAME/KEY: MISC_FEATURE
<222> LOCATION: (58)..(58)
<223> OTHER INFORMATION: X=N or T
<220> FEATURE:
<221> NAME/KEY: MISC_FEATURE
<222> LOCATION: (60)..(60)
<223> OTHER INFORMATION: X=L or D or A
<220> FEATURE:
<221> NAME/KEY: MISC_FEATURE
<222> LOCATION: (61)..(61)
<223> OTHER INFORMATION: X=S or T
<220> FEATURE:
<221> NAME/KEY: MISC_FEATURE
<222> LOCATION: (63)..(63)
<223> OTHER INFORMATION: X=V or I
<220> FEATURE:
<221> NAME/KEY: MISC_FEATURE
<222> LOCATION: (65)..(65)
<223> OTHER INFORMATION: X=D or A or S
<220> FEATURE:
<221> NAME/KEY: MISC_FEATURE
<222> LOCATION: (75)..(75)
<223> OTHER INFORMATION: X=Y or D
<220> FEATURE:
<221> NAME/KEY: MISC_FEATURE
<222> LOCATION: (79)..(79)
<223> OTHER INFORMATION: X=K or T
<220> FEATURE:
<221> NAME/KEY: MISC_FEATURE
<222> LOCATION: (82)..(82)
<223> OTHER INFORMATION: X=R or S
<220> FEATURE:
<221> NAME/KEY: MISC_FEATURE
<222> LOCATION: (83)..(83)
<223> OTHER INFORMATION: X=V or L
<220> FEATURE:
<221> NAME/KEY: MISC_FEATURE
<222> LOCATION: (84)..(84)
<223> OTHER INFORMATION: X=E or Q
<220> FEATURE:
<221> NAME/KEY: MISC_FEATURE
<222> LOCATION: (85)..(85)
<223> OTHER INFORMATION: X=A or P
<220> FEATURE:
<221> NAME/KEY: MISC_FEATURE
<222> LOCATION: (88)..(88)
<223> OTHER INFORMATION: X=L or V or F
<220> FEATURE:
<221> NAME/KEY: MISC_FEATURE
<222> LOCATION: (89)..(89)
<223> OTHER INFORMATION: X=G or A
<220> FEATURE:
<221> NAME/KEY: MISC_FEATURE
<222> LOCATION: (90)..(90)
```

```
<223> OTHER INFORMATION: X=V or T
<220> FEATURE:
<221> NAME/KEY: MISC_FEATURE
<222> LOCATION: (92)..(92)
<223> OTHER INFORMATION: X=Y or F
<220> FEATURE:
<221> NAME/KEY: MISC_FEATURE
<222> LOCATION: (94)..(94)
<223> OTHER INFORMATION: X=S or M or Q
<220> FEATURE:
<221> NAME/KEY: MISC_FEATURE
<222> LOCATION: (96)..(96)
<223> OTHER INFORMATION: X=S or A
<220> FEATURE:
<221> NAME/KEY: MISC_FEATURE
<222> LOCATION: (97)..(97)
<223> OTHER INFORMATION: X=T or Y  or L
<220> FEATURE:
<221> NAME/KEY: MISC_FEATURE
<222> LOCATION: (98)..(98)
<223> OTHER INFORMATION: X=H or Q  or N
<220> FEATURE:
<221> NAME/KEY: MISC_FEATURE
<222> LOCATION: (99)..(99)
<223> OTHER INFORMATION: X=I or T
<220> FEATURE:
<221> NAME/KEY: MISC_FEATURE
<222> LOCATION: (100)..(100)
<223> OTHER INFORMATION: X= P or S
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: MISC_FEATURE
<222> LOCATION: (105)..(105)
<223> OTHER INFORMATION: X=G or Q
<220> FEATURE:
<221> NAME/KEY: misc_feature
<222> LOCATION: (106)..(106)
<223> OTHER INFORMATION: Xaa can be any naturally occurring amino acid

<400> SEQUENCE: 112

Xaa Val Val Met Thr Gln Ser Pro Xaa Xaa Leu Xaa Xaa Xaa Xaa Gly
1               5                   10                  15

Xaa Xaa Xaa Xaa Xaa Xaa Cys Arg Xaa Ser Gln Ser Xaa Xaa Lys Xaa
            20                  25                  30

Xaa Xaa Xaa Xaa Xaa Leu Xaa Trp Xaa Xaa Gln Xaa Pro Gly Xaa Xaa
        35                  40                  45

Pro Xaa Xaa Leu Ile Tyr Xaa Xaa Ser Xaa Arg Xaa Xaa Gly Xaa Pro
    50                  55                  60

Xaa Arg Phe Ser Gly Ser Gly Ser Gly Thr Xaa Phe Thr Leu Xaa Ile
65                  70                  75                  80

Ser Xaa Xaa Xaa Xaa Glu Asp Xaa Xaa Xaa Tyr Xaa Cys Xaa Gln Ser
                85                  90                  95

Xaa Xaa Xaa Xaa Xaa Tyr Thr Phe Gly Xaa Gly Thr Lys Val Glu Ile
            100                 105                 110

Lys

<210> SEQ ID NO 113
<211> LENGTH: 5
<212> TYPE: PRT
<213> ORGANISM: Artificial Sequence
<220> FEATURE:
<223> OTHER INFORMATION: scFv linker

<400> SEQUENCE: 113

Gly Ser Gly Gly Ser
1               5
```

<210> SEQ ID NO 114
<211> LENGTH: 4
<212> TYPE: PRT
<213> ORGANISM: Artificial Sequence
<220> FEATURE:
<223> OTHER INFORMATION: scFv linker

<400> SEQUENCE: 114

Gly Gly Gly Ser
1

<210> SEQ ID NO 115
<211> LENGTH: 5
<212> TYPE: PRT
<213> ORGANISM: Artificial Sequence
<220> FEATURE:
<223> OTHER INFORMATION: scFv linker

<400> SEQUENCE: 115

Gly Gly Gly Gly Ser
1               5

<210> SEQ ID NO 116
<211> LENGTH: 15
<212> TYPE: PRT
<213> ORGANISM: Artificial Sequence
<220> FEATURE:
<223> OTHER INFORMATION: ((G4S)3 linker

<400> SEQUENCE: 116

Gly Gly Gly Gly Ser Gly Gly Gly Gly Ser Gly Gly Gly Gly Ser
1               5                   10                  15

<210> SEQ ID NO 117
<211> LENGTH: 18
<212> TYPE: PRT
<213> ORGANISM: Artificial Sequence
<220> FEATURE:
<223> OTHER INFORMATION: CD19 linker

<400> SEQUENCE: 117

Gly Ser Thr Ser Gly Ser Gly Lys Pro Gly Ser Gly Glu Gly Ser Thr
1               5                   10                  15

Lys Gly

<210> SEQ ID NO 118
<211> LENGTH: 18
<212> TYPE: PRT
<213> ORGANISM: Artificial Sequence
<220> FEATURE:
<223> OTHER INFORMATION: 18mer

<400> SEQUENCE: 118

Gly Gly Ser Ser Arg Ser Ser Ser Ser Gly Gly Gly Gly Ser Gly Gly
1               5                   10                  15

Gly Gly

<210> SEQ ID NO 119
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 119

```
Gly Gly Gly Gly Ser Gly Gly Gly Ser Gly Gly Gly Ser Gly
1               5                   10                  15

Gly Gly Gly Ser
            20
```

<210> SEQ ID NO 120
<211> LENGTH: 18
<212> TYPE: PRT
<213> ORGANISM: Artificial Sequence
<220> FEATURE:
<223> OTHER INFORMATION: linker

<400> SEQUENCE: 120

```
Lys Glu Ser Gly Ser Val Ser Ser Glu Gln Leu Ala Gln Phe Arg Ser
1               5                   10                  15

Leu Asp
```

<210> SEQ ID NO 121
<211> LENGTH: 14
<212> TYPE: PRT
<213> ORGANISM: Artificial Sequence
<220> FEATURE:
<223> OTHER INFORMATION: linker

<400> SEQUENCE: 121

```
Glu Gly Lys Ser Ser Gly Ser Gly Ser Glu Ser Lys Ser Thr
1               5                   10
```

<210> SEQ ID NO 122
<211> LENGTH: 12
<212> TYPE: PRT
<213> ORGANISM: Artificial Sequence
<220> FEATURE:
<223> OTHER INFORMATION: linker

<400> SEQUENCE: 122

```
Gly Ser Ala Gly Ser Ala Ala Gly Ser Gly Glu Phe
1               5                   10
```

<210> SEQ ID NO 123
<211> LENGTH: 8
<212> TYPE: PRT
<213> ORGANISM: Artificial Sequence
<220> FEATURE:
<223> OTHER INFORMATION: linker

<400> SEQUENCE: 123

```
Gly Gly Gly Gly Gly Gly Gly Gly
1               5
```

<210> SEQ ID NO 124
<211> LENGTH: 6
<212> TYPE: PRT
<213> ORGANISM: Artificial Sequence
<220> FEATURE:
<223> OTHER INFORMATION: linker

<400> SEQUENCE: 124

```
Gly Gly Gly Gly Gly Gly
1               5
```

<210> SEQ ID NO 125
<211> LENGTH: 6
<212> TYPE: PRT
<213> ORGANISM: Artificial Sequence

```
<220> FEATURE:
<223> OTHER INFORMATION: (His)6 Tag

<400> SEQUENCE: 125

His His His His His His
1               5

<210> SEQ ID NO 126
<211> LENGTH: 119
<212> TYPE: PRT
<213> ORGANISM: Artificial Sequence
<220> FEATURE:
<223> OTHER INFORMATION: OGD201 VH51

<400> SEQUENCE: 126

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
                20                  25                  30

Tyr Met Thr Trp Ile Arg Gln Pro Pro Arg Lys Ala Leu Glu Trp Leu
            35                  40                  45

Gly Phe Ile Arg Asn Arg Ala Asn Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 127
<211> LENGTH: 119
<212> TYPE: PRT
<213> ORGANISM: Artificial Sequence
<220> FEATURE:
<223> OTHER INFORMATION: OGD201 VH52

<400> SEQUENCE: 127

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
                20                  25                  30

Tyr Met Thr Trp Val Arg Gln Pro Pro Arg Lys Ala Leu Glu Trp Leu
            35                  40                  45

Gly Phe Ile Arg Asn Arg Ala Ser Gly Tyr Thr Thr Glu Tyr Asn Pro
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 128
<211> LENGTH: 119
```

```
<212> TYPE: PRT
<213> ORGANISM: Artificial Sequence
<220> FEATURE:
<223> OTHER INFORMATION: OGD201 VH53

<400> SEQUENCE: 128

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Ile Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 129
<211> LENGTH: 119
<212> TYPE: PRT
<213> ORGANISM: Artificial Sequence
<220> FEATURE:
<223> OTHER INFORMATION: OGD201 VH54

<400> SEQUENCE: 129

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Asp
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 130
<211> LENGTH: 112
<212> TYPE: PRT
<213> ORGANISM: Artificial Sequence
<220> FEATURE:
<223> OTHER INFORMATION: OGD201 VL54

<400> SEQUENCE: 130

Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
```

```
                20                  25                  30

Asn Gly Asn Thr Phe Leu His Trp Tyr Leu Gln Lys Ser Gly Gln Ser
            35                  40                  45

Pro Lys Leu Leu Ile Tyr Lys Val Ser Asn Arg Leu Ser Gly Val Pro
        50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 131
<211> LENGTH: 119
<212> TYPE: PRT
<213> ORGANISM: Artificial Sequence
<220> FEATURE:
<223> OTHER INFORMATION: OGD201 VH72max

<400> SEQUENCE: 131

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Ser Tyr Thr Thr Glu Tyr Ala Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115
```

<210> SEQ ID NO 132
<211> LENGTH: 119
<212> TYPE: PRT
<213> ORGANISM: Artificial Sequence
<220> FEATURE:
<223> OTHER INFORMATION: OGD201 VH49B

<400> SEQUENCE: 132

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Thr Glu Asp Thr Ala Val Tyr
                85                  90                  95
```

```
Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 133
<211> LENGTH: 119
<212> TYPE: PRT
<213> ORGANISM: Artificial Sequence
<220> FEATURE:
<223> OTHER INFORMATION: OGD201 VH49Bmax

<400> SEQUENCE: 133

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Val Ser Asn Trp Ala Phe Asp Tyr Trp Gly Gln Gly
            100                 105                 110

Thr Leu Val Thr Val Ser Ser
        115

<210> SEQ ID NO 134
<211> LENGTH: 112
<212> TYPE: PRT
<213> ORGANISM: Artificial Sequence
<220> FEATURE:
<223> OTHER INFORMATION: OGD201 VL30BH

<400> SEQUENCE: 134

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Lys Asn
            20                  25                  30

Gln Gly Asn Thr Phe Leu His Trp Phe Gln Gln Arg Pro Gly Gln Ser
        35                  40                  45

Pro Arg Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 135
<211> LENGTH: 112
<212> TYPE: PRT
<213> ORGANISM: Artificial Sequence
<220> FEATURE:
<223> OTHER INFORMATION: OGD201 VL28Bs01/A2
```

<400> SEQUENCE: 135

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Lys Ser
            20                  25                  30

Asn Ala Asn Thr Phe Leu His Trp Tyr Leu Gln Lys Pro Gly Gln Ser
        35                  40                  45

Pro Gln Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr His Ile Pro Tyr Thr Phe Gly Gln Gly Thr Lys Val Glu Ile Lys
            100                 105                 110

<210> SEQ ID NO 136
<211> LENGTH: 118
<212> TYPE: PRT
<213> ORGANISM: Artificial Sequence
<220> FEATURE:
<223> OTHER INFORMATION: OGD201 VH 72BCDR

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Leu Lys Thr Glu Asp Thr Ala Val Tyr Tyr
                85                  90                  95

Cys Ala Arg Val Ser Asn Trp Ala Phe Asp Tyr Trp Gly Gln Gly Thr
            100                 105                 110

Leu Val Thr Val Ser Ser
        115

<210> SEQ ID NO 137
<211> LENGTH: 118
<212> TYPE: PRT
<213> ORGANISM: Artificial Sequence
<220> FEATURE:
<223> OTHER INFORMATION: OGD201 72BH

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Thr Ser Glu Phe Thr Phe Ser Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala
    50                  55                  60

```
Ser Val Lys Gly Arg Phe Thr Ile Ser Arg Asp Asn Ser Lys Asn Ser
 65                  70                  75                  80

Leu Tyr Leu Gln Met Asn Leu Lys Thr Glu Asp Thr Ala Val Tyr Tyr
                 85                  90                  95

Cys Ala Arg Val Ser Asn Trp Ala Phe Asp Tyr Trp Gly Gln Gly Thr
            100                 105                 110

Leu Val Thr Val Ser Ser
        115
```

<210> SEQ ID NO 138
<211> LENGTH: 118
<212> TYPE: PRT
<213> ORGANISM: Artificial Sequence
<220> FEATURE:
<223> OTHER INFORMATION: OGD201 VH49BCDR

<400> SEQUENCE: 138

```
Glu Val Gln Leu Val Glu Ser Gly Gly Gly Leu Val Gln Pro Gly Arg
 1               5                  10                  15

Ser Leu Arg Leu Ser Cys Thr Ala Ser Glu Phe Thr Phe Thr Asp Tyr
                 20                  25                  30

Tyr Met Thr Trp Val Arg Gln Ala Pro Gly Lys Gly Leu Glu Trp Leu
             35                  40                  45

Gly Phe Ile Arg Asn Arg Ala Asn Gly Tyr Thr Thr Glu Tyr Ala Ala
     50                  55                  60

Ser Val Lys Gly Arg Phe Thr Ile Ser Arg Asp Asn Ser Lys Ser Ile
 65                  70                  75                  80

Leu Tyr Leu Gln Met Asn Leu Lys Thr Glu Asp Thr Ala Val Tyr Tyr
                 85                  90                  95

Cys Ala Arg Val Ser Asn Trp Ala Phe Asp Tyr Trp Gly Gln Gly Thr
            100                 105                 110

Leu Val Thr Val Ser Ser
        115
```

<210> SEQ ID NO 139
<211> LENGTH: 118
<212> TYPE: PRT
<213> ORGANISM: Artificial Sequence
<220> FEATURE:
<223> OTHER INFORMATION: OGD201 VH49BH

<400> SEQUENCE: 139

```
Glu Val Gln Leu Val Glu Ser Gly Gly Gly Leu Val Gln Pro Gly Arg
 1               5                  10                  15

Ser Leu Arg Leu Ser Cys Thr Thr Ser Glu Phe Thr Phe Thr Asp Tyr
                 20                  25                  30

Tyr Met Thr Trp Val Arg Gln Ala Pro Gly Lys Gly Leu Glu Trp Leu
             35                  40                  45

Gly Phe Ile Arg Asn Lys Ala Asn Gly Tyr Thr Thr Glu Tyr Asn Pro
     50                  55                  60

Ser Val Lys Gly Arg Phe Thr Ile Ser Arg Asp Asn Ser Lys Ser Ile
 65                  70                  75                  80

Leu Tyr Leu Gln Met Asn Leu Lys Thr Glu Asp Thr Ala Val Tyr Tyr
                 85                  90                  95

Cys Ala Arg Val Ser Asn Trp Ala Phe Asp Tyr Trp Gly Gln Gly Thr
            100                 105                 110

Leu Val Thr Val Ser Ser
        115
```

```
<210> SEQ ID NO 140
<211> LENGTH: 112
<212> TYPE: PRT
<213> ORGANISM: Artificial Sequence
<220> FEATURE:
<223> OTHER INFORMATION: OGD201 VL28BH

<400> SEQUENCE: 140

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Lys Asn
            20                  25                  30

Asn Ala Asn Thr Phe Leu His Trp Tyr Leu Gln Lys Pro Gly Gln Ser
        35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Ile Pro Tyr Thr Phe Gly Gly Gly Thr Lys Val Glu Ile Lys
            100                 105                 110
```